United States Patent
Chang et al.

(10) Patent No.: US 6,370,964 B1
(45) Date of Patent: Apr. 16, 2002

(54) DIAGNOSTIC LAYER AND METHODS FOR DETECTING STRUCTURAL INTEGRITY OF COMPOSITE AND METALLIC MATERIALS

(75) Inventors: Fu-Kuo Chang; Mark Lin, both of Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 09/447,480

(22) Filed: Nov. 23, 1999

Related U.S. Application Data

(60) Provisional application No. 60/109,562, filed on Nov. 23, 1998.

(51) Int. Cl.[7] .................................................. G01D 7/00
(52) U.S. Cl. .................................................. 73/862.046
(58) Field of Search .................. 73/760, 763, 767, 73/772, 855, 862.041, 862.046

(56) References Cited

U.S. PATENT DOCUMENTS

| | | | |
|---|---|---|---|
| 3,978,731 A | * 9/1976 | Reeder et al. ................. | 73/703 |
| 4,359,720 A | * 11/1982 | Chai et al. .................... | 341/26 |
| 4,779,452 A | 10/1988 | Cohen-Tenoudji et al. | |
| 4,843,891 A | * 7/1989 | Burnner, et al. ........ | 73/862.046 |
| 4,921,415 A | 5/1990 | Thomas, II et al. | |
| 5,184,516 A | 2/1993 | Blazic et al. .................. | 73/799 |
| 5,195,046 A | * 3/1993 | Gerardi et al. ................ | 702/35 |
| 5,401,922 A | * 3/1995 | Asta ............................ | 200/5 A |
| 5,814,729 A | 9/1998 | Wu et al. ...................... | 73/588 |
| 5,869,189 A | 2/1999 | Hagwood, IV et al. ..... | 428/461 |
| 6,006,163 A | 12/1999 | Lichtenwalner et al. ...... | 702/36 |

OTHER PUBLICATIONS

International Search Report for PCT/US00/41839, which is the PCT application of this US application.

* cited by examiner

*Primary Examiner*—Max Noori
(74) *Attorney, Agent, or Firm*—Lumen Intellectual Property Services, Inc.

(57) ABSTRACT

A diagnostic layer having a network of actuators and sensors may be incorporated into or on the surface of composite, metallic, and laminated materials for monitoring the structural health of the material. The diagnostic layer is adapted for detecting and measuring changes in the condition of the material, e.g., the site and extent of damage in the material. In a preferred embodiment, piezoelectric devices are embedded in the diagnostic layer in a network, and serve as actuators and sensors. Signals emitted from the sensors in response to physical deformation, either by an impact or as a result of stress waves generated by the actuators, are diagnostic of the current condition of the diagnostic layer. The diagnostic layer is also adapted to monitor the curing process of a composite material and accurately determine when curing is complete. Methods for monitoring changes in conditions of a material are also disclosed.

26 Claims, 19 Drawing Sheets

Sensor Spectrogram

Scatter Spectrogram

DIAGNOSTIC LAYER AND METHODS FOR DETECTING STRUCTURAL INTEGRITY OF COMPOSITE AND METALLIC MATERIALS

CROSS-REFERENCE TO RELATED APPLICATIONS

This application is based on Provisional application No. 60/109,562 filed Nov. 23, 1999, which is herein incorporated by reference.

GOVERNMENT INTEREST

This invention was made with U.S. Government support under Contract No. DAAH04-95-1-0611-P00001, awarded by the U.S. Army Research Office. The U.S. Government may have certain rights in this invention.

BACKGROUND OF THE INVENTION

1. Field of the Invention

This invention relates to a layer with an embedded network of distributed sensors and actuators that can be surface-mounted on or embedded in a structure for monitoring its structural condition and for detecting anomalies in the hosting metallic or nonmetallic (composite) structures. In particular, the layer can be embedded in composite structures for monitoring curing progression and impact load and for detecting delamination failure and damage. The layer can also be surface-mounted on metallic structures for detecting delamination, crack generation and propagation.

2. Background of the Related Art

Nearly all in-service structures require some form of maintenance for monitoring their integrity and health condition to prolong their life span or to prevent catastrophic failure of these structures. Current schedule-driven inspection and maintenance techniques can be time-consuming, labor-intensive and expensive. The existing visual inspection techniques are often inadequate to identify a damage state invisible to the human eye, such as delaminations in composite structures. However, the current non-destructive evaluation techniques, such as ultrasonic and eddy current scanning, acoustic emission, and X-ray inspection, although useful for inspection of isolated locations, are impractical in many cases in terms of downtime and human involvement such as field inspection of in-service structures.

Recent advances in smart structure technologies and material/structural damage characterization combined with recent developments in sensors and actuators have resulted in a significant interest in developing new diagnostic techniques for in-situ characterization of material properties during manufacturing, for monitoring structural integrity, and for detection of damage to both existing and new structures in real time with minimum human involvement.

In order to develop such techniques, the structures considered must be equipped with a builtin network of a large array of sensors and actuators. There are currently no effective techniques for implementing a large array of sensors and actuators into existing or new structures economically and efficiently. Although piezoelectric materials have been considered for use as sensors and actuators, they are treated individually in installation and implementation. They must be individually placed on the hosting structures, leaving all the connection wires hanging out from the structures. Because of the way in which piezoelectric elements are installed, each element must be calibrated separately.

A system for in-situ delamination detection in composites is disclosed in U.S. Pat. No. 5,814,729, issued to Wu et al. The system consists of piezoelectric actuators and fiber optic sensors embedded within a laminated composite structure. The actuators generate vibration waves that propagate through the structure, and the sensors sense these strain waves, generating signals. Damping characteristics of the waves are calculated from the signals, and delamination regions can be determined. This system has a number of drawbacks. First, it is not designed for accommodation of a large array of piezoelectric actuators. Each sensor and actuator must be placed individually, leaving the wiring and calibration problems listed above unsolved. Second, the fiber optics are used as sensors only. The method of detecting damage, known as "line-of-sight" or "through-transmission," requires the damage to lie exactly in the path of an actuator-sensor pair for it to be detected. Damage in surrounding regions cannot be detected using the system of Wu et al. Thus, the method of Wu et al. cannot be applied to the installation of a large sensor network, and uses only fiber optics for sensors and piezoelectric materials as actuators.

A self-contained conformal circuit for structural health monitoring and assessment is described in U.S. Pat. No. 5,184,516, issued to Blazic et al. The system consists of a series of stacked layers and traces for sensing strain and cracks in a surface. Flexible circuits are used to create the electrical interconnects. The entire structure is then affixed to the surface of a material being tested, after which testing occurs. This system has a number of limitations. It is only useful for monitoring conditions in the plane of the conformal circuit, i.e. the surface structure, and not interior structure of a laminated material. Information about internal damage, including delamination, cannot be obtained. In addition, the conformal circuit can only collect information at discrete points (i.e. the location of crack and strain gauges). The area between sensors cannot be monitored. Information about existing damage can also not be obtained. In addition, acoustic emission sensors are passive sensors-they indicate damage but cannot locate it without further information.

U.S. Pat. No. 5,869,189, issued to Hagood, IV et al., discloses composites for structural control that can be used for both actuating and sensing deformations. The composite includes a series of flexible, elongated piezoelectric fibers arranged in a planar, parallel array and separated by a relatively soft polymer. The composite can be embedded within a structural component, with the fibers extending along the length or width of the component. Multiple layers of the composite can be used to generate complex deformations. Because of the geometry of the fiber placement (i.e. parallel arrays), it is difficult to sense and locate deformations that occur only within a small region of the component. The fibers can extend along the entire length and width of the composite, and it is intended more for sensing larger scale bending and vibration than for detecting delamination or damage at a particular location.

There are no existing techniques available for efficiently and economically integrating a large networked array of sensors and actuators into existing or new structures for real-time monitoring of structural integrity and/or for detecting damage in the structures.

OBJECTS AND ADVANTAGES

Accordingly, it is an object of the present invention to provide a layer containing a network of a large array of built-in sensors and actuators with an integral diagnostics capability for incorporation into both existing and new structures made of both metallic (such as aluminum alloys) or nonmetallic (fiber-reinforced composites) materials.

It is another object of the invention to provide a layer that is capable of monitoring the structural health of an object on an on-going basis without requiring disassembly and without the need to take equipment out of service.

It is an additional object of the invention to provide a diagnostic layer that can be calibrated before being embedded into a structure, so that minimal software changes are required after the structure is manufactured.

It is a further object of the invention to provide a diagnostic layer that allows for easy embedding of sensors and actuators into fiber-reinforced composite structures during manufacturing.

It is an additional object of the invention to provide a method of monitoring the curing process during manufacture of a laminate material, thereby saving time, money, and energy during laminate manufacturing.

It is a further object of the invention to provide a method for determining the force-time history of an impact on a structure.

Finally, it is an object of the invention to provide a technique for identifying an area of damage in a composite material having an integral diagnostic layer.

The invention provides the following advantages:

Real-time monitoring and reporting of structural conditions, saving in maintenance costs Minimum human involvement in structural diagnostics, reducing labor and downtime Automation and self-diagnostics, enhancing safety and reliability

SUMMARY OF THE INVENTION

These and other objects and advantages are attained by a diagnostic layer for incorporation into composite and metallic structures, including laminate structures. The layer contains sensors and actuators and is capable of diagnosing physical deformations or mechanical stress within the layer on a continual basis. When embedded in a laminate structure, the layer can also accurately determine the point at which the curing process of the laminate structure is complete.

The diagnostic layer is used to detect a structural condition of a material and includes a thin dielectric substrate, a plurality of sensors spatially distributed on the substrate, and a plurality of conductive elements in the substrate for electrically connecting the sensors to an output lead. The sensors are capable of generating electrical signals representative of a structural condition of the substrate, and are preferably piezoelectric sensors, which generate electrical signals in response to physical deformations of the sensors. The layer can also include at least one actuator, and preferably a plurality of actuators spatially distributed on the substrate and also connected to the output lead by the conductive elements. Preferably, the sensors and actuators are not distinct; piezoelectric materials act as both sensors and actuators.

The diagnostic layer may also be incorporated into a diagnostic system for detecting a structural condition. This condition may be the location and size of damage in a structure, location and force of an impact to the structure, or the quality of manufacturing of embedded structures such as composite materials, including the progression of curing of a laminate material. In addition to the layer, the system contains a signal receiver unit electrically coupled to the output lead for receiving output signals from the sensors. This coupling may be by wireless means. The system may also have a signal generating unit electrically connected to the output lead for providing an input signal to the actuators. Also included in the system is an interface unit in electrical communication with the signal receiver unit and, preferably, the signal generating unit. The interface unit preferably includes: a processor unit for processing data from the signal receiver unit to detect the structural condition; a control unit for controlling the input signal to the signal generating unit; and a memory unit for storing the data from the signal receiver unit.

The present invention also provides a method of detecting a change in the condition of a structure containing a diagnostic layer as described above. The method includes the following steps: providing a hosting structure containing the diagnostic layer; transmitting a first input signal to an actuator of the diagnostic layer through the output lead; receiving a first set of output signals from the sensors in response to the first input signal; at a later time, inputting a second signal to the actuator; receiving a second set of output signals from the sensors in response to the second signal; and analyzing the first set of output signals and the second set of output signals to determine a difference between the two. This difference represents the change in structural condition of the material, which may be a location and size of damage, or progression of curing. The output signals may also be processed to generate data representative of first and second structural conditions of the material. Subsequent $n^{th}$ signals may also be sent and received for a predetermined time to monitor further changes between an $n^{th}$ set of output signals and a prior set of output signals. The diagnostic layer may be inside a composite material, or it may be bonded to an external surface of metallic or composite materials.

A method for detecting a physical deformation of a structure, preferably the force and location of an impact to the material, is similar to the above method. The method has the steps of receiving a signal from at least one of the sensors, in which the signal represents physical deformation of the sensor; and processing the signal to generate data representing physical deformation of the material.

Finally, a method of curing a laminate composite is provided. The method includes the steps of: providing an uncured composite material having a diagnostic layer; subjecting the uncured composite material to an elevated temperature that initiates curing of the material; and monitoring changes in the condition of the diagnostic layer of the composite material until the condition of the diagnostic layer is substantially constant. Preferably, the diagnostic layer is as described above, and signals are sent to the actuators and received from the sensors. When the received signals are constant, the curing is complete.

DETAILED DESCRIPTION OF THE PREFERRED EMBODIMENTS

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

Figure 1A:
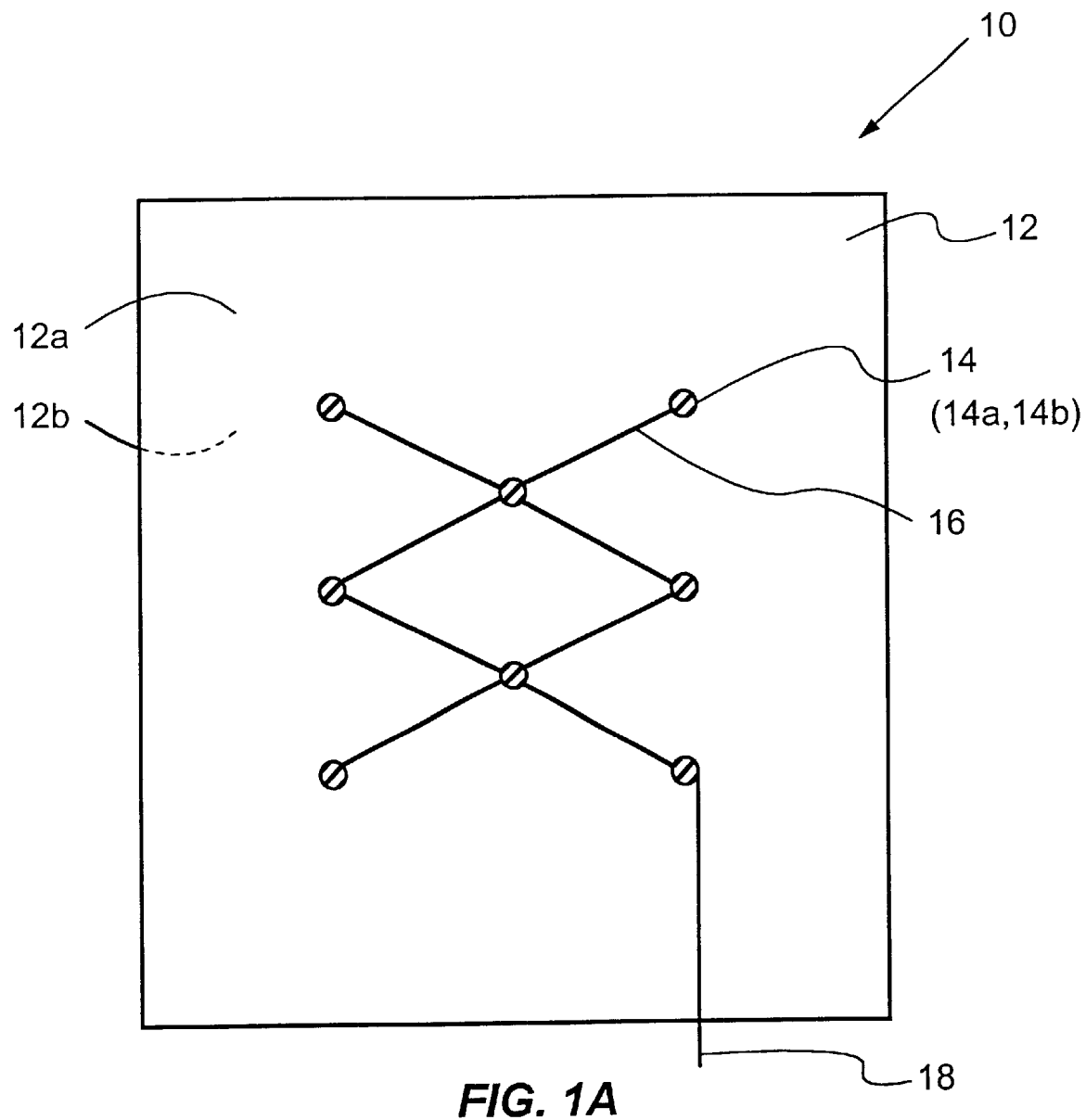
FIG. 1A schematically represents a diagnostic layer in face view, according to one embodiment of the invention.

With reference to the drawings, FIG. 1A schematically represents a diagnostic layer 10, including a plurality of actuators/sensors 14 arranged on or in a dielectric substrate 12. Actuators/sensors 14 are connected to each other via a conductive element or wire 16. According to a preferred embodiment, actuators/sensors 14 are arranged on diagnostic layer 10 as a network. Preferably dielectric substrate 12 includes upper and lower layers 12a, 12b, respectively, of dielectric material, and conductive element 16 is sandwiched therebetween. An electrical output lead 18 is electrically connected to a network of the plurality of actuators/sensors 14. Lead 18 allows the input of suitable signals from an external device (not shown) to actuators/sensors 14 (actuators 14a), as well as output of signals from actuators/sensors 14 (sensors 14b). Diagnostic layer 10 is also known as a Stanford Multi-Actuator-Receiver Transduction (SMART) layer.

Figure 1B:
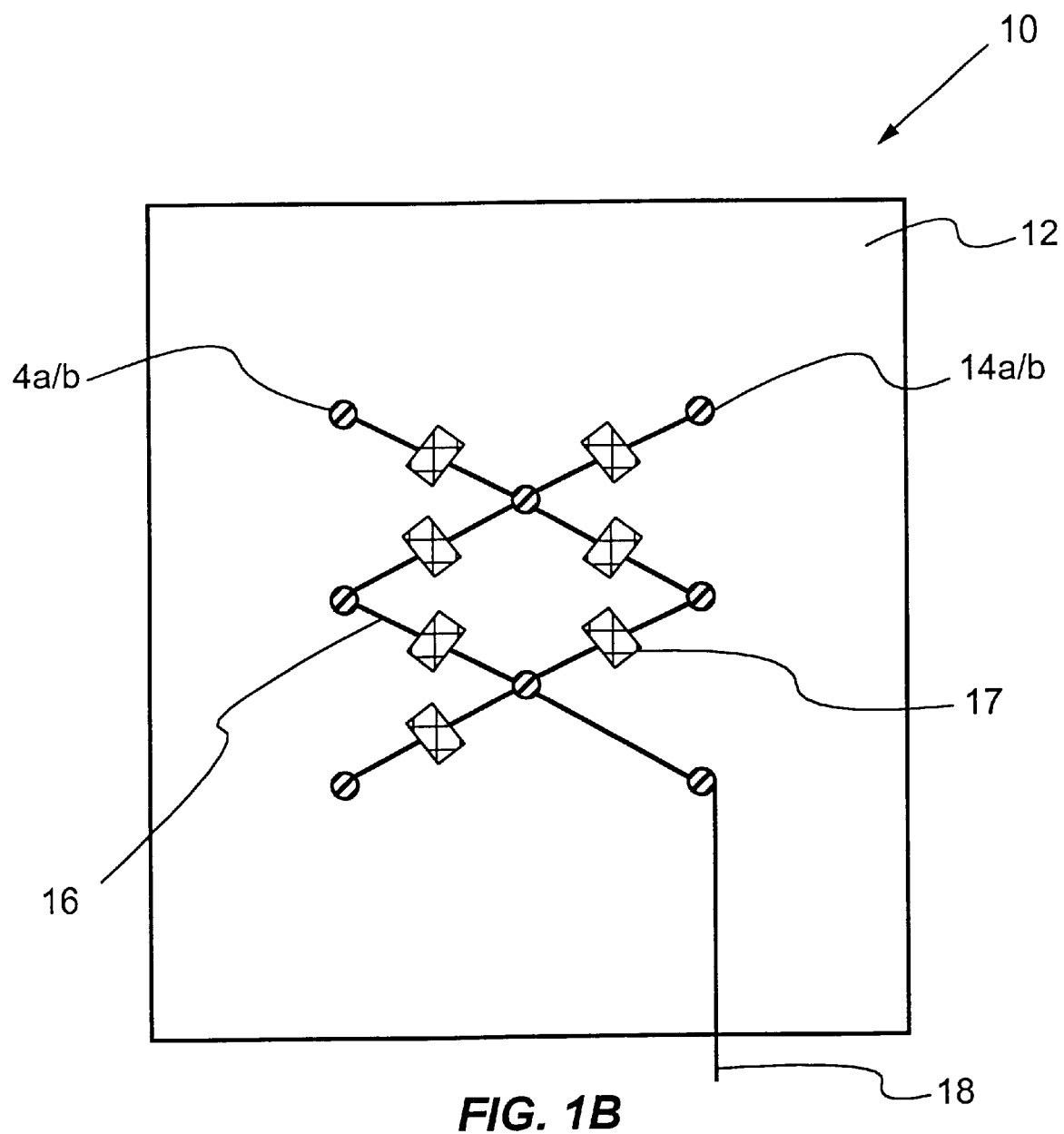
FIG. 1B shows a face view of a diagnostic layer, including a plurality of microswitches in the circuitry of the layer, according to another embodiment of the invention.

According to one embodiment of the invention, each actuator/sensor has its own conductive element or wire 16. In this instance, for a segment of diagnostic layer 10 having ten actuators/sensors 14, there are ten conductive elements or wires 16. According to an alternative embodiment, as shown in FIG. 1B, diagnostic layer 10 may incorporate microswitches 17 in the circuitry, whereby signals can be channeled around the array of actuators/sensors 14, allowing for a reduction in the number of wires 16 per actuator/sensor 14.

Figure 5A:
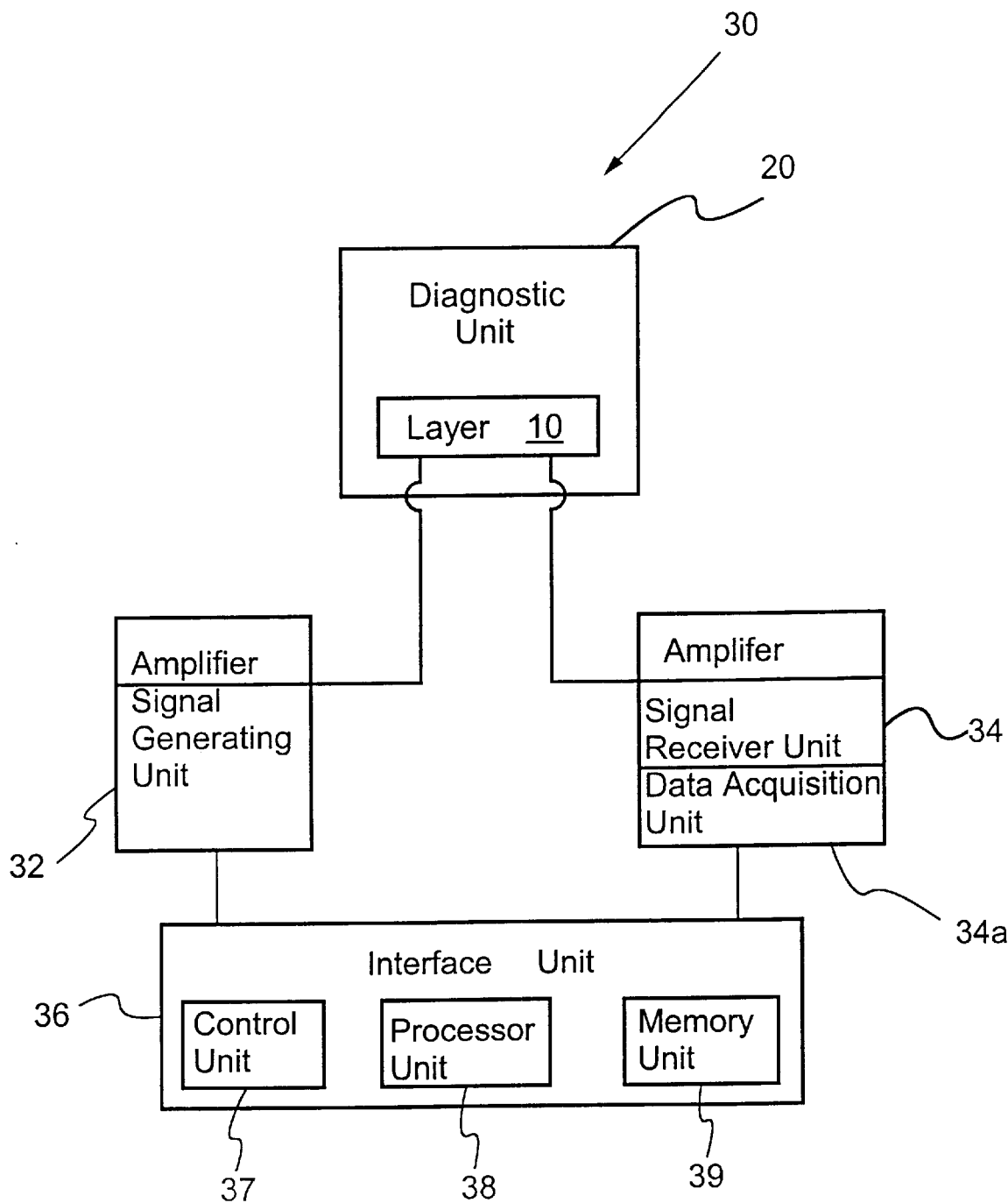
FIG. 5A is a block diagram that schematically shows the relationship between components of a diagnostic system, according to the invention.
Figure 5B:
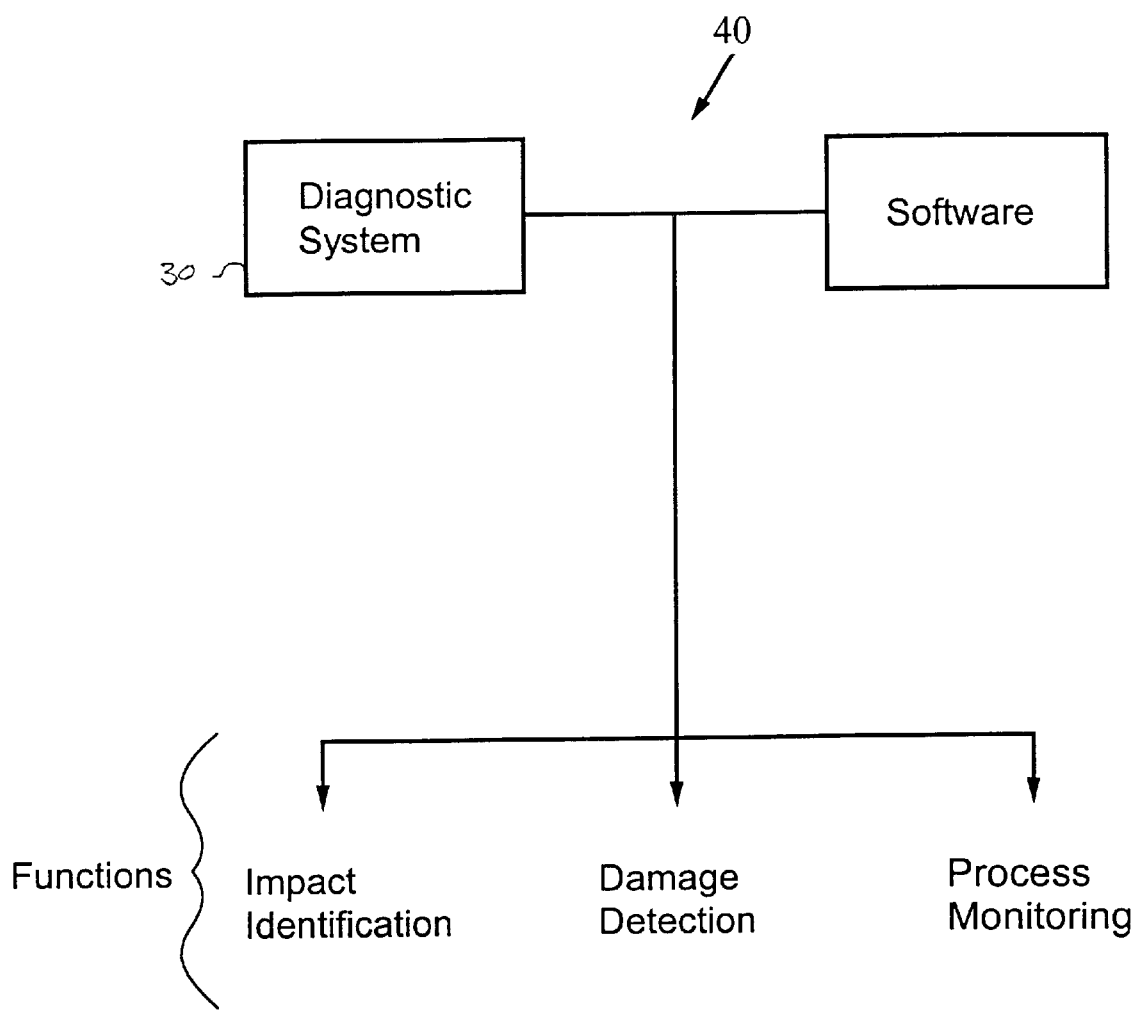
FIG. 5B schematically represents the relationship between a diagnostic system and suitable computer software to provide a multi-functional structural monitoring system including a diagnostic layer, according to the invention.
Figure 6:
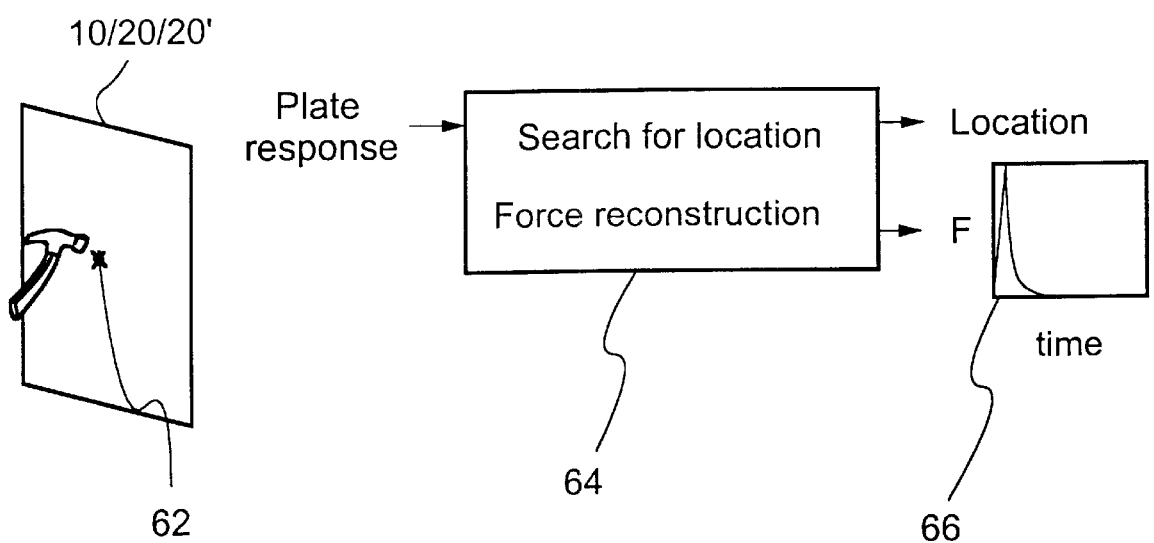
FIG. 6 is a schematic representation of how the location and force-time history of an impact on a surface of a laminate panel containing a diagnostic layer can be determined by suitable software, according to the invention.

A currently preferred dielectric substrate 12 is Kapton® polyimide film (DuPont, Circleville, Ohio). However, other polymeric dielectric films or like materials may also be used. Actuators/sensors 14 may be two separate dissimilar components. For example, each of the plurality of actuators/sensors 14 may include an actuator 14a and a sensor 14b. Alternatively, each actuator/sensor 14 may be a single component, in which case the sensors and actuators are said to be not distinct from one another. According to a currently preferred embodiment, each actuator/sensor 14 is a piezoelectric device which may function as both an actuator 14a and as a sensor 14b. An actuator/sensor 14 may function as an actuator 14a at one point in time, and thereafter the same actuator/sensor 14 may be switched to function as a sensor 14b. Switching may be performed either by hardware (switches) (not shown), or by suitable software used to interface with layer 10 (FIGS. 5B, 6). Note that if actuator/sensor 14 acts as both an actuator 14a and a sensor 14b, the same resolution may be achieved with half as many devices as for a system with distinct actuators 14a and sensors 14b.

A piezoelectric device functioning as an actuator 14a and/or as a sensor 14b may be in the form of a piezoelectric (polymer) film, a piezoelectric crystal, or a piezoelectric ceramic. A currently preferred actuator/sensor 14 of the invention is a piezoceramic device.

A piezoelectric actuator/sensor 14, such as a piezoceramic, physically deforms upon application of an electrical signal. In addition, application of a mechanical force to the piezoceramic causes a physical deformation that generates an electrical signal. This behavior allows a single piezoceramic to act both as a sensor 14b and as an actuator 14a. Inputting a time-varying electrical signal to any one of actuators/sensors 14 causes a propagating stress wave or propagating mechanical deformation to emanate from the sensor/actuator 14 and travel through the material. A plurality of neighboring actuators/sensors 14 may then detect this propagating stress wave. The nature of the wave received by any given neighboring actuator/sensor 14 is a function of the spatial arrangement of that actuator/sensor 14 in relation to the actuator/sensor 14 which emitted the wave. The sensor 14b converts the propagating stress wave into electromagnetic signals (e.g. voltage) that are indicative of the condition of layer 10. Alternately, an impact applied to layer 10 causes a physical deformation of layer 10 and actuators/sensors 14. As a result, sensors 14b emit electrical signals indicative of the force of the impact. In turn, signals emanating from sensors 14b, which are indicative of the condition of layer 10, may be received by a signal receiving unit 34 (FIG. 5A) coupled to layer 10, e.g., via lead 18.

Note that in contrast to prior art devices incorporating piezoelectric fibers, actuators/sensors 14 of the present invention can be thought of as point sensors and actuators. That is, the stress wave generated by an actuator 14a in response to an input signal is not generated over a region, but can be considered to propagate from a single point. Similarly, a sensor 14b generates electrical signals representative of the overall deformation of sensor 14b, and not deformations in particular locations of sensor 14b.

The spatial distribution or arrangement of the plurality of actuators/sensors 14 on diagnostic layer 10 is, to some extent, a matter of design choice. Thus, the preferred spatial arrangement may depend on a number of factors, for example, the size of the panel, laminate, or structure in which layer 10 is embedded, the intended application of the structure, and the sensitivity level required for monitoring the structure. For aeronautical and astronautical applications, the distances between each of the plurality of actuators/sensors 14 will normally be in the range of from about 2 to 30 inches, more preferably from about 4 to 20 inches, and most preferably from about 5 to 12 inches.

Diagnostic layer 10 having an array of actuators/sensors 14 provides a uniform response over the entire network of actuators/sensors 14. That is to say, an impact with a given force at different locations on layer 10 gives the same magnitude of response; and an impact of a given force repeated at the same location of layer 10 gives the same response in terms of both magnitude and location. Diagnostic layer 10 is essentially calibrated at manufacture, and subsequent recalibration is unnecessary.

Figure 1C:
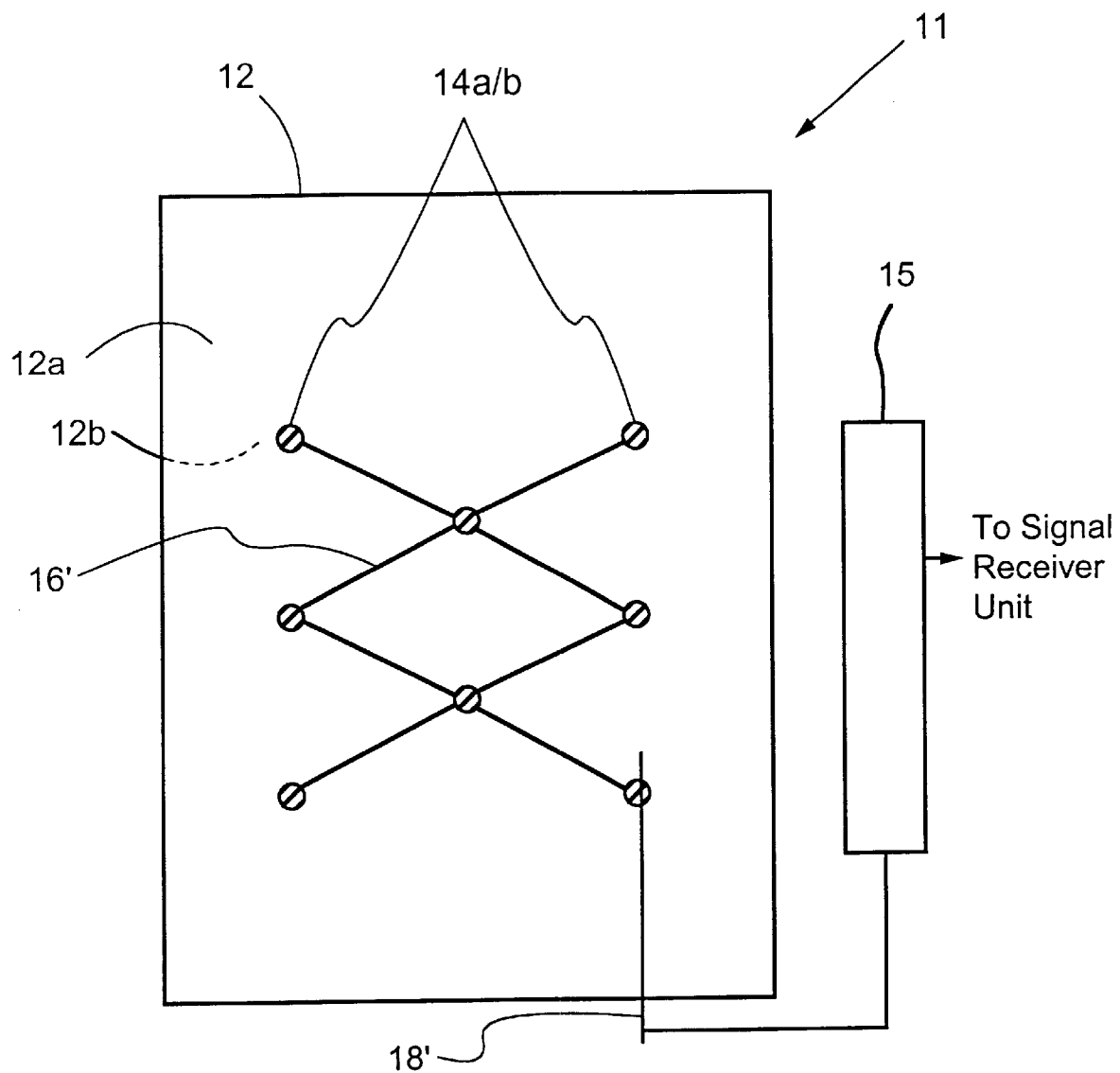
FIG. 1C schematically represents in face view a diagnostic layer having an external wireless transmitter, according to another embodiment of the invention.

FIG. 1C shows a diagnostic layer 11 in face view, according to another embodiment of the invention. Layer 11 has several features in common with the embodiment depicted in FIG. 1A, including a plurality of actuators/sensors 14 arranged on or in dielectric substrate 12. Actuators/sensors 14 are connected to each other via a conductive element or wire 16. Preferably, actuators/sensors 14 are arranged on diagnostic layer 11 as a network. Preferably dielectric substrate 12 includes upper and lower layers 12a, 12b of dielectric material, and conductive element 16 is sandwiched therebetween. An electrical lead 18 is electrically connected to each of the plurality of actuators/sensors 14. Lead 18 allows the input of suitable signals from an external device (not shown) to actuators/sensors 14. Lead 18 also allows transfer of signals from sensors 14b to a transmitter 15, which then transmits the signals to a signal receiver unit 34 (FIG. 5A). This embodiment illustrates a variation of the more general design that uses wireless communication to establish a link between the diagnostic layer 11 and the signal receiver unit 32 via transmitter 15. The wireless communication is preferably in the form of radio signals but may also be infrared signals, microwave signals or other electromagnetic radiation signals. Wireless communication is particularly useful if the operating conditions of the laminate material make wired connections difficult or impossible. Except as otherwise noted herein, what has been stated regarding layer 10 of FIG. 1A applies equally to layer 11 of FIG. 1C.

The following discussion specifically details the use of diagnostic layer 10 of the present invention in a laminated, composite material. However, it will be appreciated that layer 10 may be used inside non-laminated composite materials and metals, and on the external surface of composites and metals. When used on the surface, layer 10 may be applied to existing structures. When incorporated into new structures, layer 10 is embedded during manufacturing.

Figure 2A:
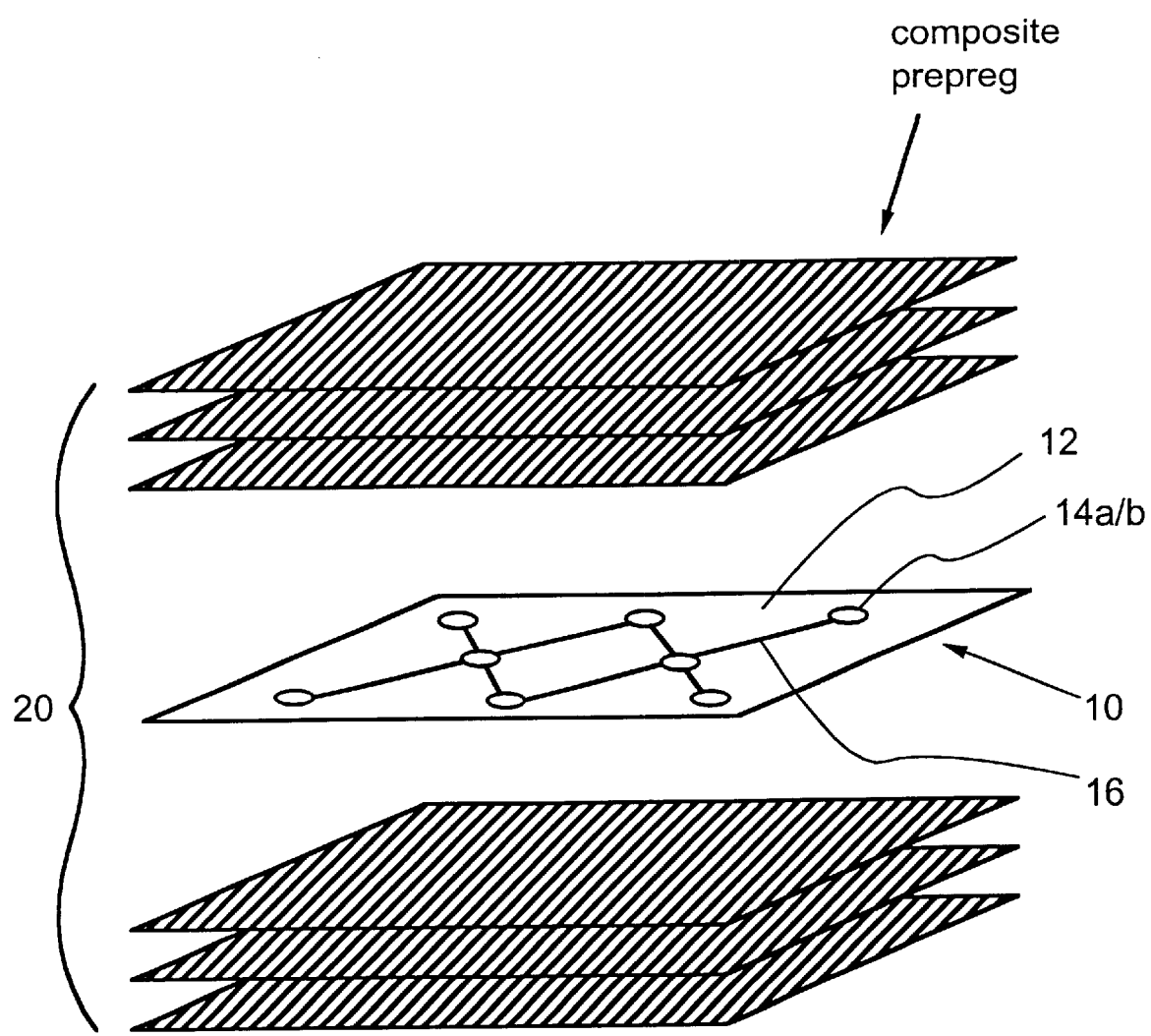
FIG. 2A is a perspective view schematically representing the incorporation of a diagnostic layer into a composite laminate, according to another embodiment of the invention.

FIG. 2A schematically represents the incorporation of diagnostic layer 10 between composite prepregs in a composite to provide a diagnostic laminate unit 20, according to the invention. In this instance, diagnostic layer 10 is structurally equivalent to an additional layer of laminate unit 20. For example, diagnostic layer 10 may be bonded to other layers within laminate unit 20, and cured at high temperature. Laminates 20 having diagnostic layer 10 incorporated therein do not show any decrease in strength as gauged by shear tests and flat-wise tension tests, as compared with laminates lacking layer 10, as is described below with reference to FIGS. 8 and 9.

Composite prepregs often contain highly conductive carbon fibers. For example, Gr/Ep (graphite fiber/epoxy resin) is a common composite material used in laminated structures. For proper operation of diagnostic layer 10, conductive elements 16 must be electrically isolated from such carbon fibers. Sandwiching conductive elements 16 between upper and lower layers 12a and 12b of dielectric material accomplishes this purpose. On the other hand, actuators/sensors 14 must be connected to an electrical ground, and the carbon fibers of adjacent prepreg layers can be used as the ground. If the prepreg layers contain neither carbon fibers nor other conductive materials, an additional conductive layer must be placed over actuators/sensors 14 to act as the ground.

Figure 2B:
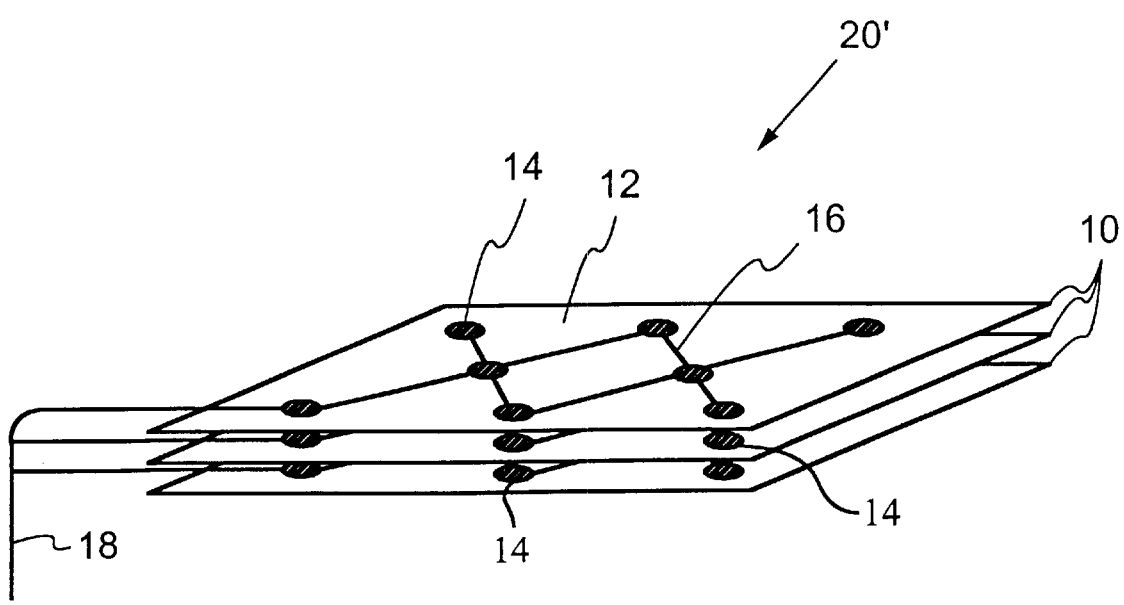
FIG. 2B shows a schematic representation of a plurality of diagnostic layers combined to form a multi-layer diagnostic unit, according to another embodiment of the invention.

According to another embodiment of the invention, schematically depicted in FIG. 2B, a plurality of diagnostic layers 10 may also be combined to form a laminate, multi-layer diagnostic unit 20'. Diagnostic unit 20' may be incorporated in a laminate panel in a manner analogous to the incorporation of layer 10 in laminate unit 20 of FIG. 2A. A plurality of diagnostic layers 10 may also be spatially distributed through the thickness of the laminate to establish inter-layer communication. Sensors 14b from one layer may be used to receive diagnostic signals generated by actuators 14a on another layer. Apart from incorporation of layer 10 in laminate materials, layer 10 may also be bonded to the exterior surface of various structural components. For example, layer 10 may be bonded to the exterior of metal or non-metal composite panels (not shown). Note that layer 10 can be used for both existing structures, by postbonding onto the surface, as well as for new structures by integrating layer 10 inside the material during manufacturing.

Whether layer 10 is incorporated within a laminate (e.g., 20), or on the exterior of a panel, the operation or function of layer 10 is essentially the same, namely built-in actuators 14a generate diagnostic signals that are received by built-in sensors 14b. Diagnostic signals received from sensors 14b can be interpreted, for example, by suitable software, to provide diagnostic information on the condition of layer 10 itself or laminate 20/20' which incorporates layer 10. Thus, built-in diagnostics can indicate whether layer 10/laminate 20/20' is damaged/undamaged or cured/uncured. The manner in which actuators 14a and sensors 14b interact with each other, and with external devices, to provide diagnostic information on layer 10 is described fully below.

Figure 3A:
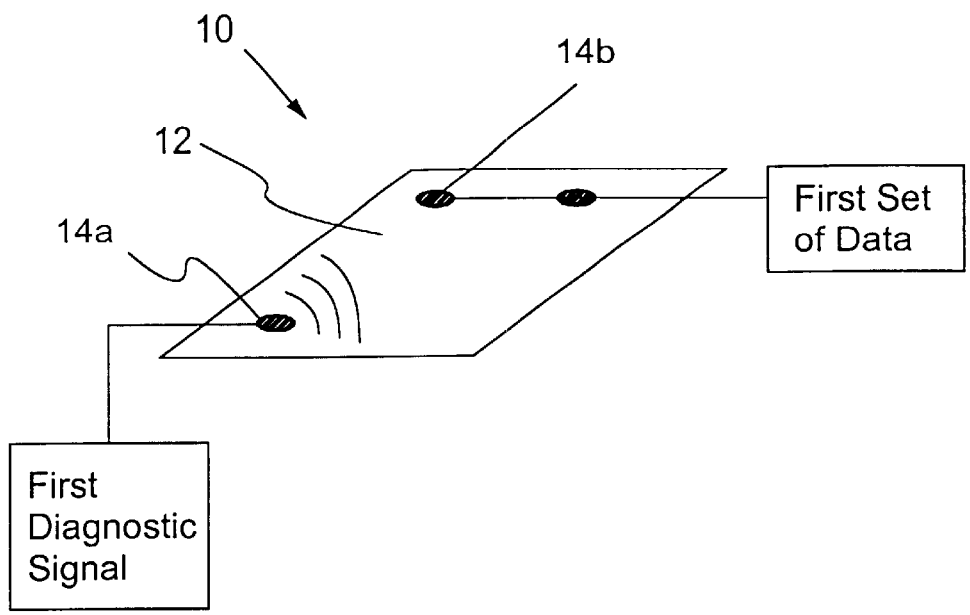
FIGS. 3A–3B schematically represent the detection by a diagnostic layer of the location and size of damage sustained by a panel incorporating the diagnostic layer, according to another embodiment of the invention.
Figure 3B:
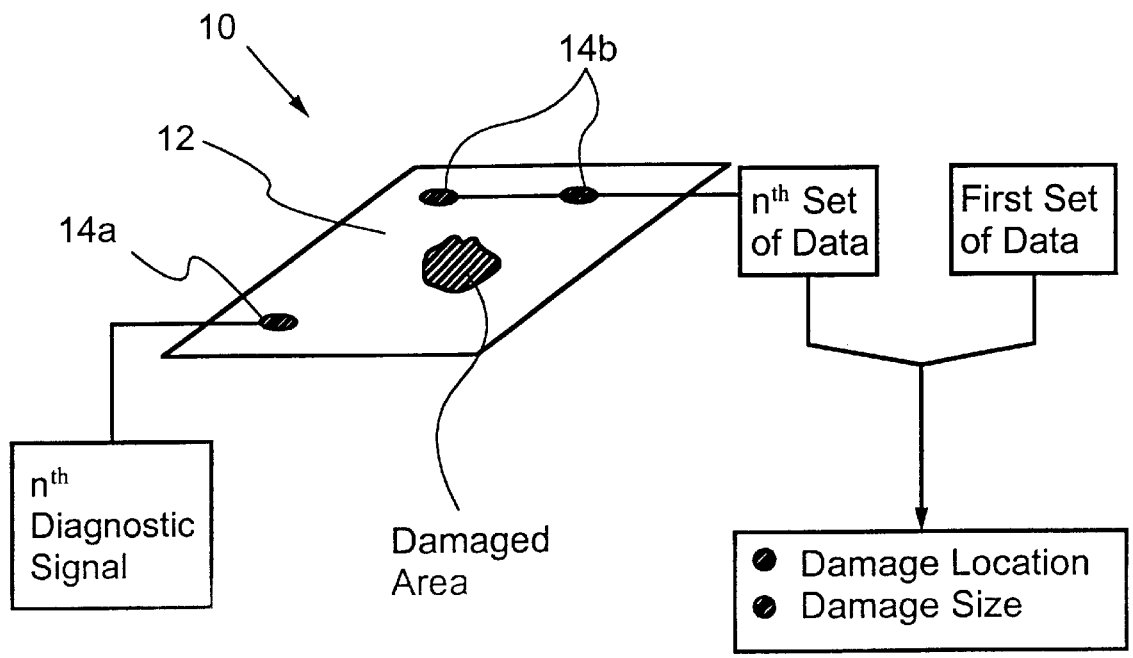

FIGS. 3A–B schematically represent the detection by diagnostic layer 10 of the location and size (or extent) of damage sustained by diagnostic layer 10, or laminate panel 20/20' (FIGS. 2A–B), according to another embodiment of the invention. With reference to FIG. 3A, in which layer 10 is in a first state or condition at a first time point, e.g., undamaged (or uncured), a first input signal from an external device (not shown) causes actuator 14a of layer 10 to emit a first signal (i.e. stress wave) which is received by a plurality of sensors 14b. For the sake of clarity, two sensors 14b are shown in FIGS. 3A, 3B. The signals received by the plurality of sensors 14b maybe combined to provide a first set of data. The first set of data is characteristic or diagnostic of the first condition of layer 10, and may be stored in a memory unit 39 (FIG. 5A), e.g., of a computer. FIG. 3B depicts a situation in which a subsequent input signal from an external device (not shown) causes actuator 14a to emit a subsequent stress wave which is also received by a plurality of sensors 14b. If the condition of layer 10 has changed from the first condition (e.g., if damage has been sustained to give damaged layer 10', or if laminate 20 has been cured), the combined signal received by the plurality of sensors 14b will also have changed accordingly, and corresponds to a subsequent set of data which may also be stored. Based on the differences between the first and subsequent set of data the location and extent of damage sustained by damaged layer 10' (or laminate 20) may be determined, e.g., by the use of a suitable computer program.

Figure 4A:
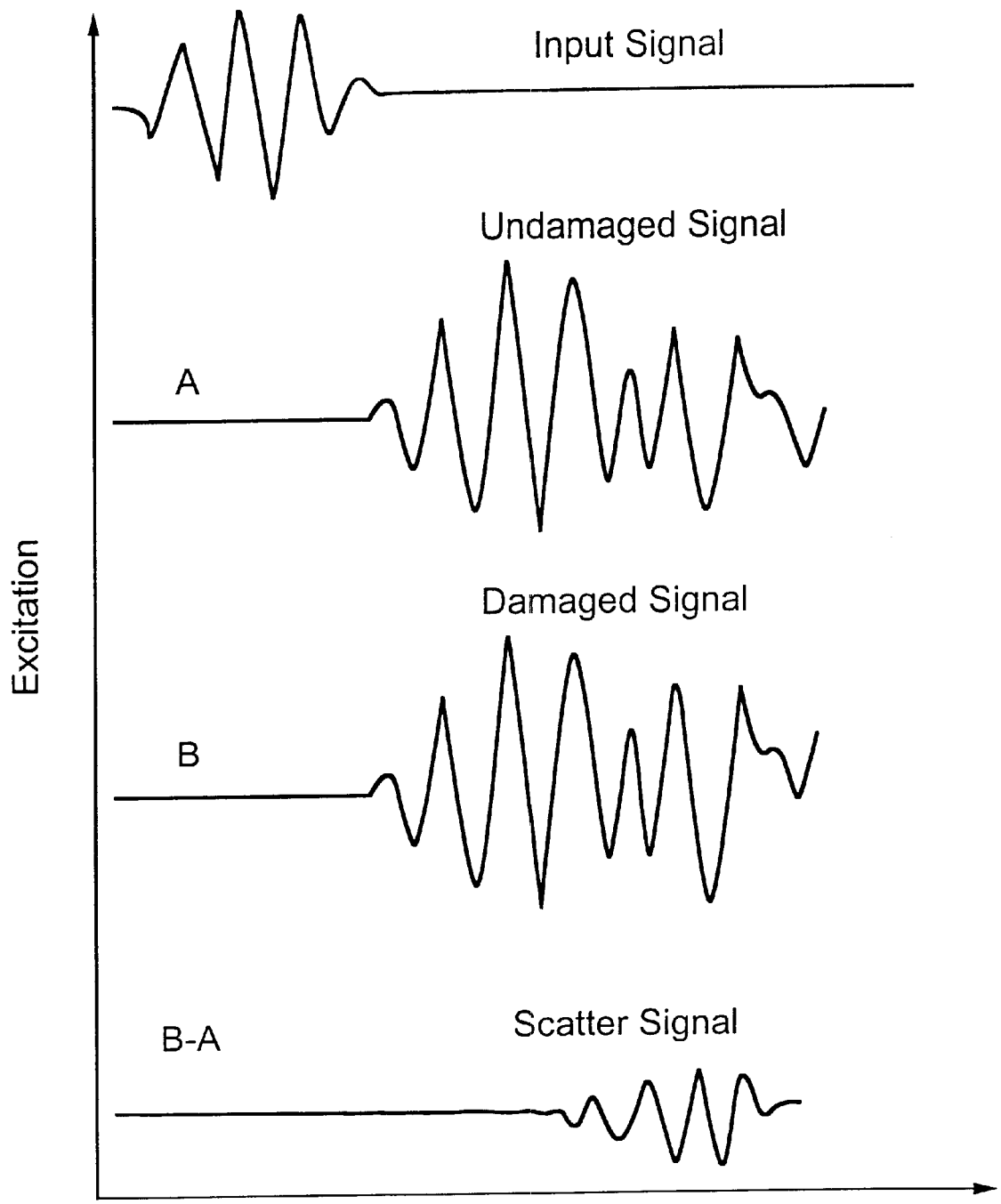
FIG. 4A shows an input signal (I) to an actuator of a diagnostic layer, and excitation due to signals received by sensor(s) with the diagnostic layer in the undamaged state (A), in the damaged state (B), as well as the scatter signal (B-A), according to the invention.

In FIGS. 3A and 3B, input signals are shown to a single actuator 14a. In practice, however, inputs may be made to a plurality of actuators 14a, or to the entire sum of actuators 14a in a given panel or structure of layer 10/laminate 20. One or more waves propagating from each of the plurality of actuators 14a may be received by a plurality of sensors 14b, thereby creating a plurality of paths. Ordinarily, the ratio of the number of sensors receiving waves propagating from a given actuator to the number of paths created is 1:1. Signals from each sensor/path may be combined to provide a set of data, which may be stored, and which is representative of a condition of the panel or structure being monitored, essentially as described above. A plurality of subsequent sets of data may be collected at various time intervals during the entire life cycle of a panel or structure which contains layer 10, as will be described herein. Subsequent sets of data may be stored in the memory of a computer. The difference between a first or prior set of received signals and a subsequent ($n^{th}$) set of received signals may be recorded as the wave scatter (FIG. 4A). The wave scatter is therefore indicative of a change in condition, e.g., damage sustained, of diagnostic layer 10. The scatter signal for all paths, at a given time, may be interpreted by suitable software and a computer to provide an overall reading of the structural health or condition of a given laminate structure (FIGS. 5B, 6). For example, the size and location of damage sustained to a laminate panel (e.g., 20, 20') may be determined. Note that this method provides both wave scatter (i.e., wave reflected by the damage) and through-transmission information, and does not require the damage to lie along the path of an actuator-sensor pair to be detected.

Signals input to actuators 14a of layer 10 from a device external to layer 10 (e.g., from signal input unit 32 of FIG. 5A) may take the form of voltage, current of other electromagnetic signals. According to a currently preferred embodiment of the invention, signals input to actuators 14a are in the form of a pulse wave consisting of a five-peak waveform (i.e. 5-peak sine wave, also referred to as a modulated sine wave, FIG. 4A, Input Signal) at a frequency of 30 to 250 kHz.

Signals received by sensors 14b in response to signals input to actuators 14a may take the form of stress waves (i.e. propagating mechanical energy). Signals received by sensors 14b from actuators 14a are preferably in the same frequency range as the input frequencies, and most preferably in the range from 30 kHz to 250 kHz.

Signals output from sensors 14b and received by a device external to layer 10 (e.g., signal receiver unit 34, FIG. 5A) may take the form of voltage, current or other electromagnetic properties. According to a currently preferred embodiment of the invention, signals received from sensors 14b are in the form of voltage measurements.

Using damage to layer 10 as an example of a change in condition (and hence a change in diagnostic signal), FIG. 4A shows an input signal (I) inputted to actuator(s) 14a of layer 10. A representative output diagnostic signal from sensors 14b before damage to layer 10 is represented by the trace labeled A (Undamaged Signal). A representative output signal from sensors 14b after damage to layer 10 is represented by the trace labeled B (Damaged Signal). A Scatter Signal B-A is the difference between the undamaged and damaged output signals, and is representative of the extent (size) and location of any damage sustained by layer 10.

Figure 4B:
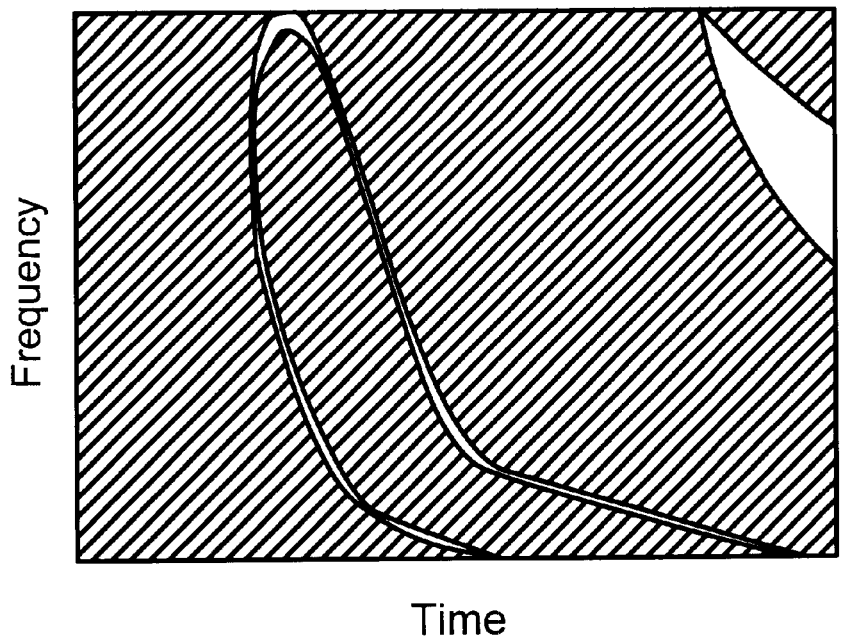
FIGS. 4B–4C show examples of a sensor spectrogram and a scatter spectrogram, respectively, according to the invention.
Figure 4C:
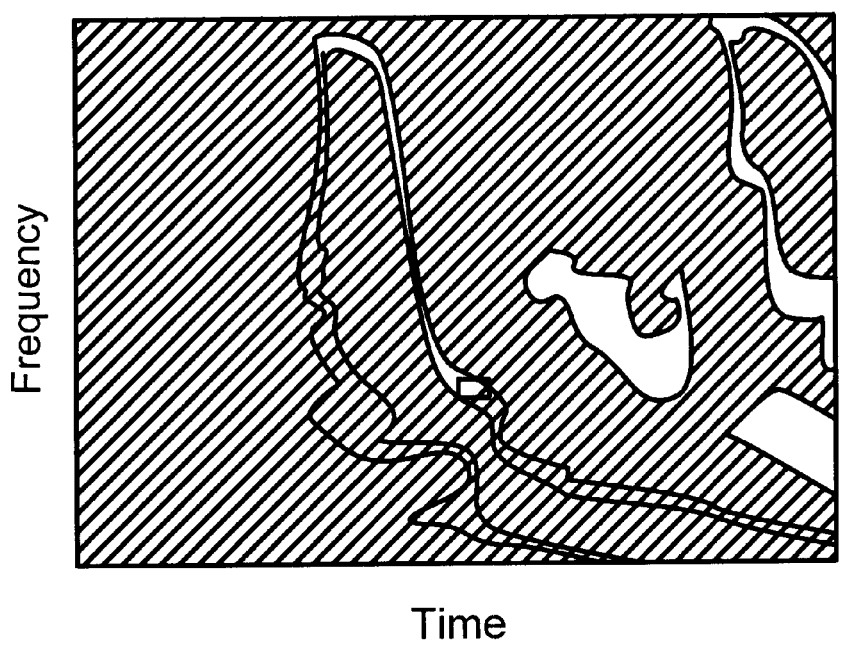

Examples of a sensor spectrogram and a scatter spectrogram obtained from a diagnostic layer 10 of the invention are shown in FIGS. 4B–4C. Sensor spectrograms and scatter spectrograms may be obtained by scanning the output diagnostic signal from sensors 14b of layer 10 over a wide frequency range. Sensor spectrograms and scatter spectrograms are three-dimensional plots, and can also be represented as two-dimensional contour plots, similar to topographical maps. A sensor spectrogram is a reflection of how the wave of a diagnostic input signal (e.g., from a signal input unit 32, FIG. 5A) is propagated throughout diagnostic layer 10. A scatter spectrogram reflects the nature of damage or change in condition of layer 10 or a laminate structure 20/20' incorporating layer 10. In a situation where no change in condition (no damage) has occurred to layer 10, the scatter spectrogram may appear blank. Interpreting spectrograms as shown in FIGS. 4B–4C is known in the art.

FIG. 5A schematically represents a diagnostic system 30 for diagnosing changes in, or monitoring the condition of, a diagnostic laminate unit 20. Unit 20 includes diagnostic layer 10 electrically coupled to a signal generating unit 32 for providing input signals to actuators 14a of layer 10. A currently preferred generating unit 32 is a function generator, such as a Model 33120A-15 MHz function/arbitrary wave generator from Hewlett Packard Company of Palo Alto, Calif. Diagnostic system 30 further includes a signal receiver unit 34, electrically coupled to diagnostic layer 10 for receiving output signals from sensors 14b. A data acquisition unit 34a is typically part of signal receiver unit 34. The data acquisition unit 34a is in electrical communication with an interface unit 36 for interfacing with unit 20. Interface unit 36 preferably includes a control unit 37 for controlling signal input to layer 10 via generating unit 32; a processor unit 38 for processing data from receiver unit 34; and a memory unit 39 for storing data received from processor unit 38 or signal receiver unit 34. Processor unit 38 may include a computer and suitable software for signal processing and interpretation routines related to signals received from sensors 14b of layer 10. Further, there may be two amplifiers, one for each of generating unit 32 and receiver unit 34, depending on the output/input capabilities of the respective units. For example, the Hewlett Packard 33120A function generator can only output a maximum of 10 volts, and so a voltage amplifier is typically used in conjunction with this device. The amplifiers may be separate components or may be integrated into units 32 and 34.

Figure 14:
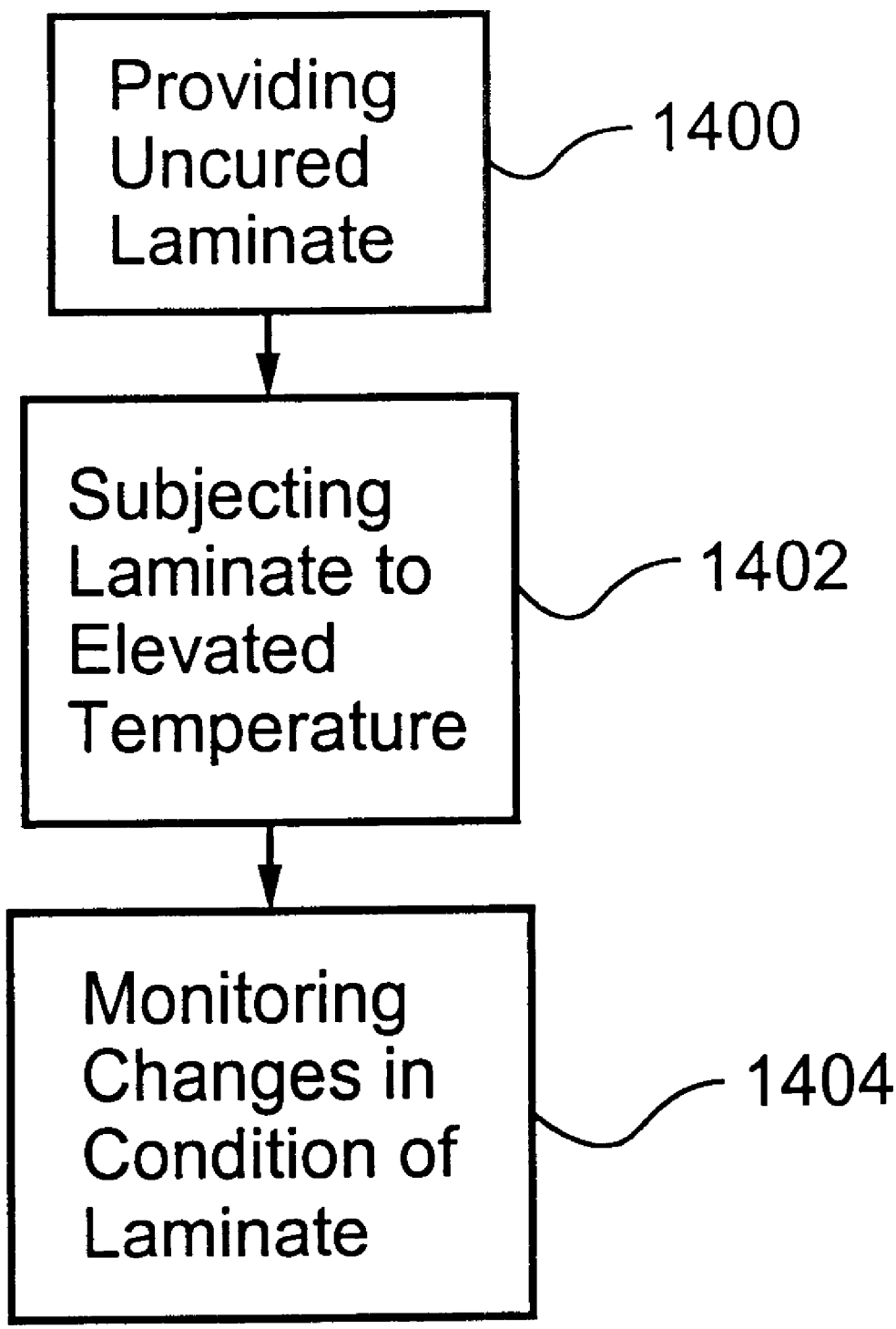
FIG. 14 schematically represents steps involved in a method of curing a laminate material having a diagnostic layer, according to another embodiment of the invention.

FIG. 5B schematically represents the interaction of diagnostic system 30 with suitable software to provide a multifunctional structural monitoring system 40. Functions of system 40 include, but are not limited to, impact identification and damage detection of various structures, as well as monitoring of laminate curing processes. Thus system 40 may function to identify the location of impacts, the time the impacts occur, and the force of the impacts that occur on layer 10 or on a structure containing layer 10. System 40 may also be used to detect the size and location of damage that has been sustained by layer 10 or a structure containing layer 10. System 40 may further be used to monitor changes occurring in a laminate structure 20/20' during the curing process of the laminate structure, as is described fully below (FIG. 14).

An example of software which has been successfully integrated with system 30 of the invention is known as IDIMPACT code. This software provides not only diagnosis of an impact location on layer 10, but also an analysis of force-time history following a foreign object impact on layer 10. IDIMPACT is described further in M. Tracy, "Impact Load Identification for Composite Plates Using Distributed Piezoelectric Sensors," Ph.D. Dissertation, Aeronautics and Astronautics, Stanford University, 1996, and in M. Tracy and F. K. Chang, "Identifying Impact Load in Composite Plates Based on Distributed Piezosensors," Proceedings of the SPIE Smart Structures and Materials Conference, San Diego, Calif., 1996.

FIG. 6 schematically represents the role of computer code (e.g., IDIMPACT) in determining the location of an impact, and in recreating a force-time history of the impact on a surface of diagnostic layer 10 or on a surface of a laminate diagnostic unit 20/20' containing diagnostic layer 10. Following an impact 62 to layer 10 or unit 20/20' from a foreign object (in this example, a hammer blow), the response of actuators/sensors 14 of layer 10 (located on or within structure 20/20') may be analyzed with the aid of suitable software 64 and a computer (not shown), to obtain information about the location of damage resulting from impact 62. In addition, the force of the impact over time can be reconstructed as a force-time plot (66). Note that for detecting impact, signal input to actuators 14a is unnecessary. Physical deformation is provided by the impact itself, and not by strain waves propagating from actuators 14a in response to an input signal. In the case of impact detection, only the sensing function of actuators/sensors 14 is employed.

Figure 7A:
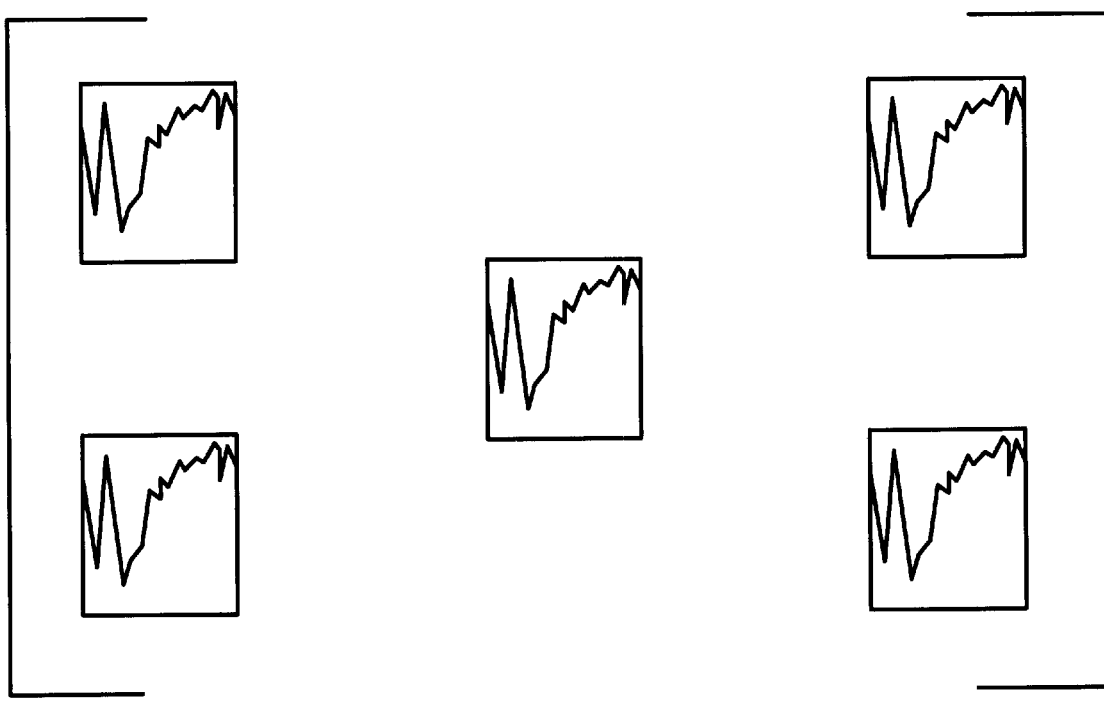
FIG. 7A shows piezoelectric sensor measurements for five sensors of a diagnostic layer embedded in a laminate panel subjected to impact from a hammer, according to the invention.

FIG. 7A schematically represents piezoelectric sensor measurements from five piezoceramic sensors 14b of diagnostic layer 10 of a laminate structure 20/20' subjected to impact from a hammer blow (FIG. 6). Each of the five plots (microstrain vs. time in milliseconds) corresponds to data from one sensor 14b. The data from each sensor 14b is obtained as a voltage response. However, for analytical purposes the voltage data from each sensor is converted to express the mechanical strain of layer 10 at the particular location of each sensor 14b. Sensor voltage and strain are directly related: strain on layer 10 at each sensor location may be calculated by multiplying the voltage measurement of that sensor by a scaling factor (microstrain=$10^{-6}$∈). The impact force may be reconstructed based on the combined measurements of a plurality of sensors 14b after impact/damage has been sustained by layer 10. Sensor measurements prior to an impact are not required to determine the location, time, or force of the impact; only the sensor measurements taken at the time of impact and after impact are needed.

Figure 7B:
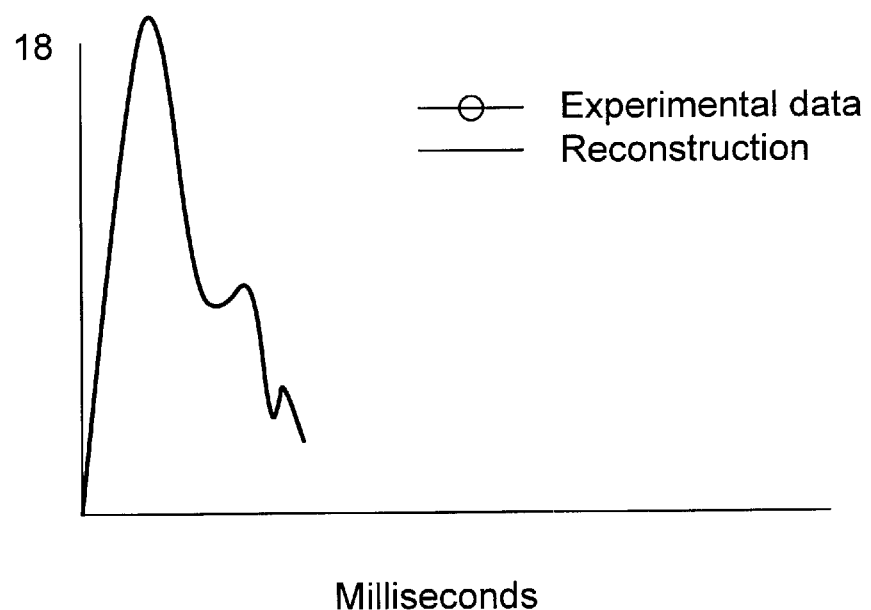
FIG. 7B shows a force-time plot of the impact as determined by diagnostic layer sensor measurements (FIG. 7A), according to the invention, as compared with a plot of the same impact as determined by a modally tuned impulse hammer incorporating a force sensor.

FIG. 7B is a force-time plot representing a reconstruction of the history of the impact (hammer blow) sustained by layer 10/laminate 20/20' (FIG. 6) based on measurements (FIG. 7A) from sensors 14b, according to the invention. A force-time plot of the same impact (hammer blow) was determined experimentally using a modally tuned impulse hammer having a force sensor, as is well known in the art. The instrument was a model 086C04 (PCB Piezotronics, Inc., Depew, N.Y.). When the force-time plot predicted by the diagnostic system 30 of the invention (Reconstruction) is compared with measurements obtained from the PCB model 086C04 modally tuned impulse hammer (Experimental Data), a close correlation is observed, as is apparent from FIG. 7B. This close correlation illustrates the accurate diagnostic capability of the invention, both in monitoring damage to a structure 10/20/20', and in determining the nature of an impact responsible for causing the damage.

The data obtained according to FIG. 7A, and plotted in FIG. 7B, were obtained in an environment having artificially induced high ambient noise levels. A high noise environment was used in order to assess the capabilities of the invention to function under conditions which simulate the type of environment in which the invention may be used in commercial practice (e.g., in the presence of engine noise from a vehicle, aircraft, or naval vessel). Clearly, the invention is accurate under these conditions.

Figure 8:
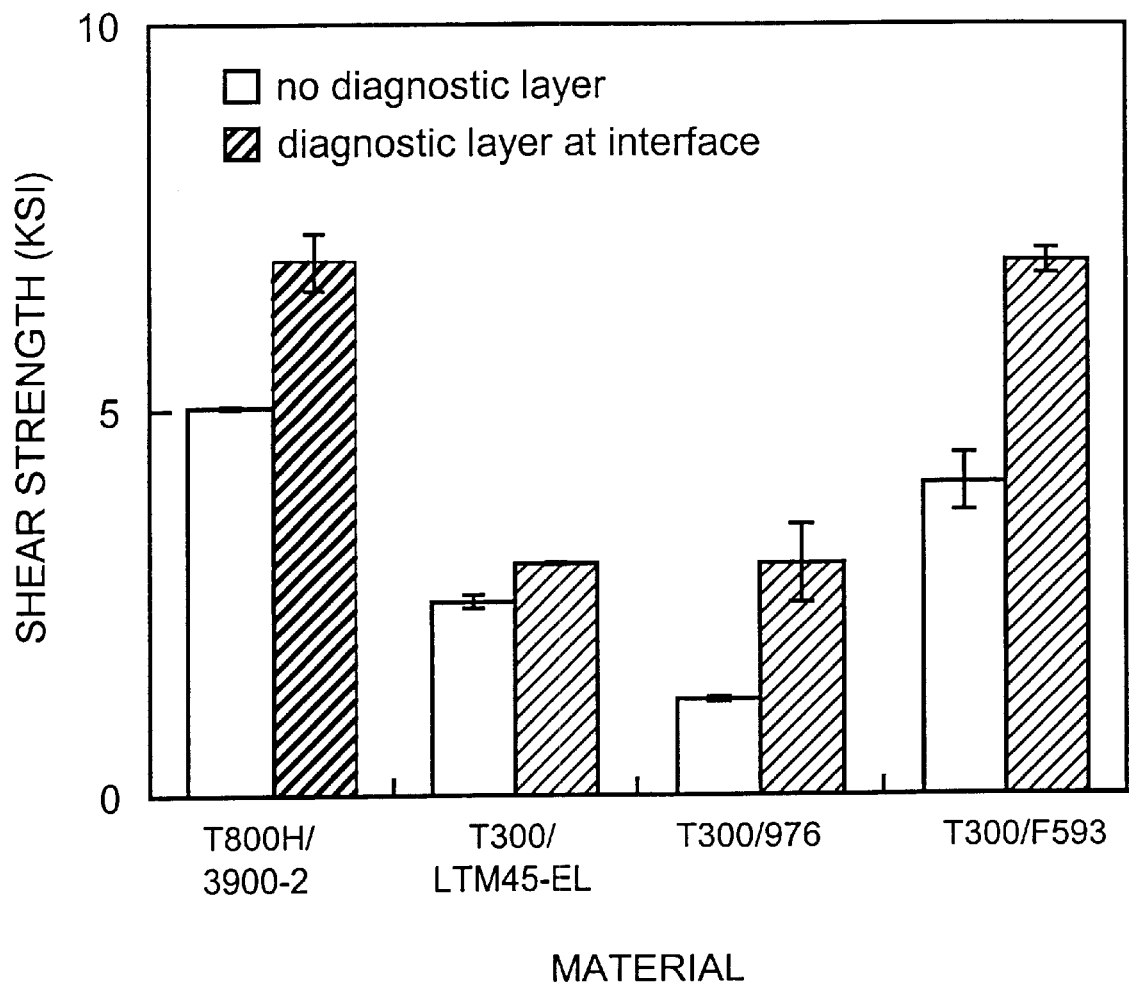
FIG. 8 is a histogram comparing the strength of shear-lap joints for laminates with and without a diagnostic layer at the joint interface, according to the invention.

Laminate materials incorporating a diagnostic layer 10 were subjected to mechanical tests to assess the integrity and strength of a diagnostic laminate 20. FIG. 8 is a histogram comparing the strength of shear-lap joints for four different laminate materials, with and without diagnostic layer 10 at a joint interface. The four different materials are labeled in FIG. 8. Each lap-joint specimen was co-cured in an autoclave. It can be seen from FIG. 8 that the incorporation of diagnostic layer 10 did not result in decreased bond strength at the interface of the composites.

Figure 9:
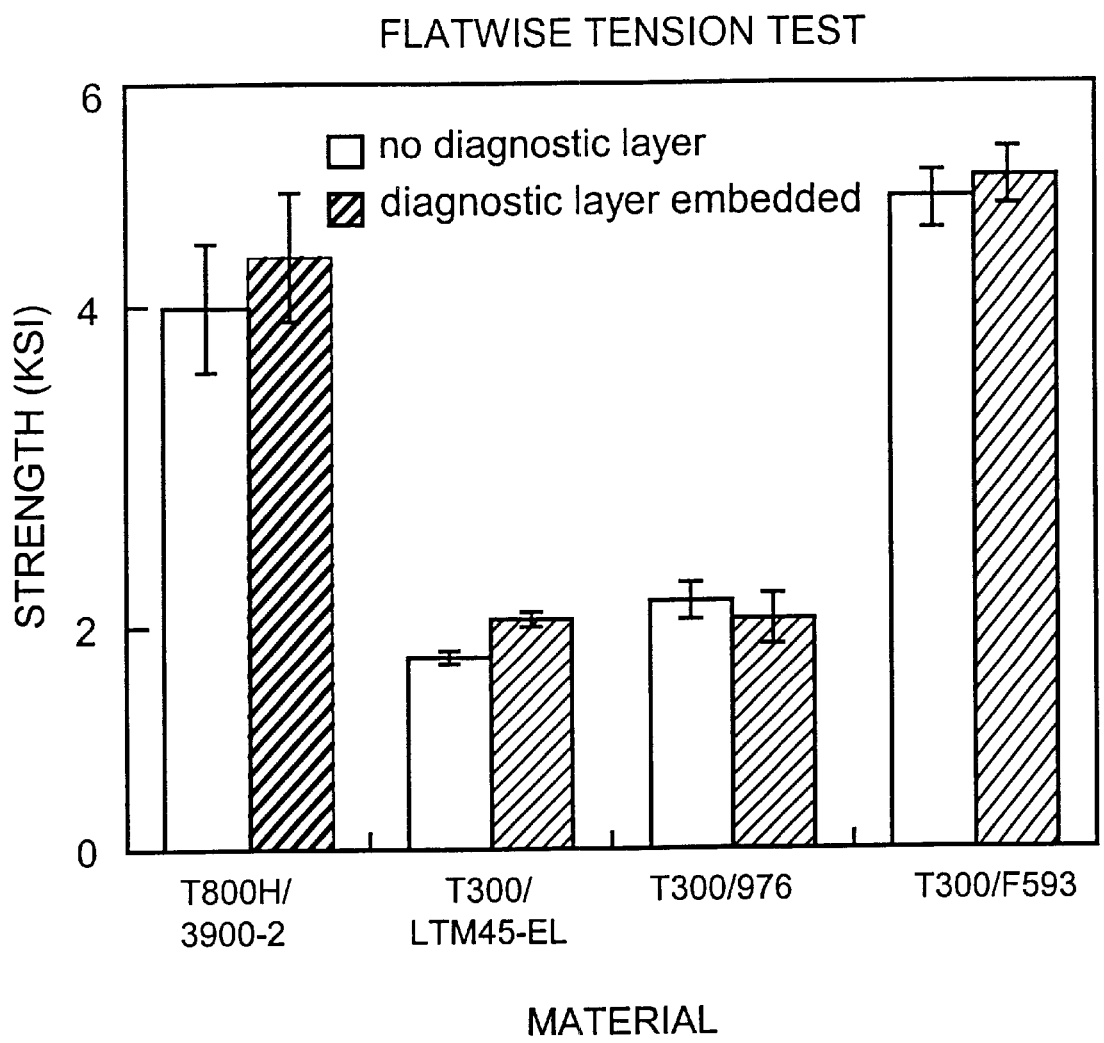
FIG. 9 is a histogram comparing flat-wise tensile strength of laminates with and without a diagnostic layer; according to the invention.

FIG. 9 is a histogram comparing flat-wise tensile strength of the same four composites, with and without diagnostic layer 10 incorporated therein. For each of the four laminate materials which included diagnostic layer 10, failure occurred within the composite, and not at the diagnostic layer interface nor within diagnostic layer 10. It is evident from these results that the inclusion of diagnostic layer 10 does not reduce the out-of-plane tensile strength of these laminates.

Figure 10:
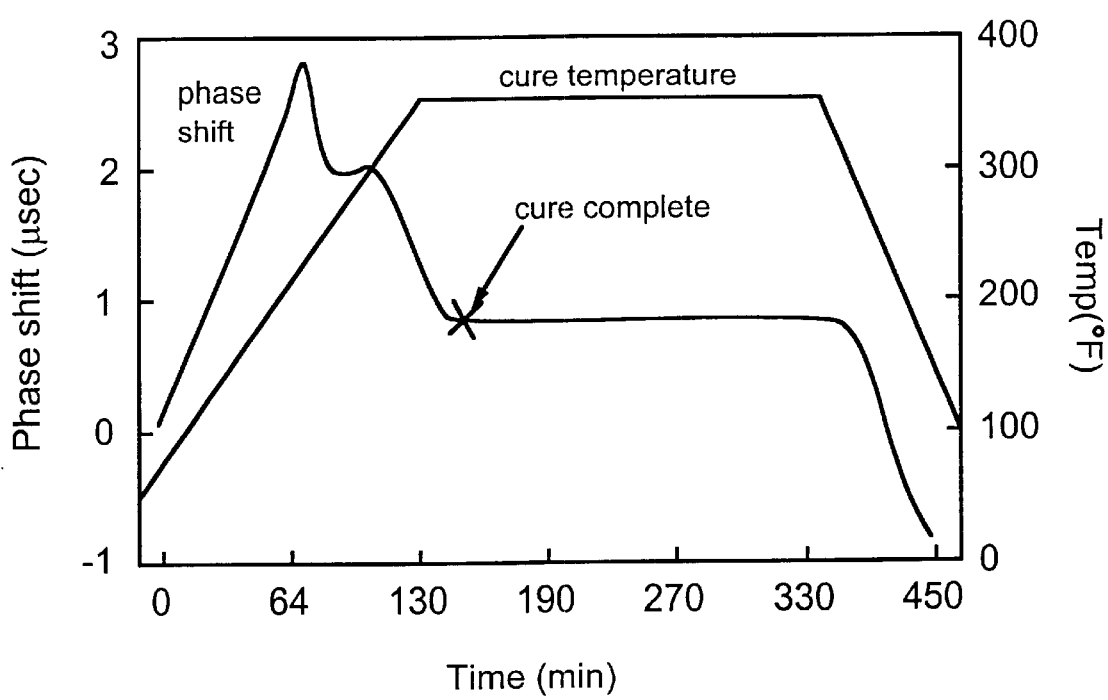
FIG. 10 shows the phase delay of a diagnostic wave during the curing cycle of laminate materials, according to another embodiment of the invention.

During manufacture of composite or laminate materials using prior art methods, curing is performed by heating the laminate for a period of up to several hours at temperatures rising to in excess of 300° F. in an autoclave. The condition of laminate materials changes during the curing process. Using prior art laminate materials and manufacturing methods, there is no reliable technique for in-situ monitoring of changes in the condition of the laminate materials during the curing process. In contrast, in the case of a laminate material having diagnostic layer 10 of the invention, the progression of curing can be monitored by means of signals input to, and received from, diagnostic layer 10. FIG. 10 shows a plot of phase delay of a received diagnostic signal relative to the signal received at time zero, the start of the cure cycle of a laminate material having diagnostic layer 10. When the temperature begins to rise, the phase delay of a diagnostic wave increases sharply initially, and then declines to attain a substantially constant level. The maximum and constant values for phase shift and the exact shape of the curve tend to vary depending on the particular laminate material undergoing the curing process. However, the basic shape of the curve is as shown in FIG. 10.

The phase delay is a measure of change in the condition of the laminate which contains layer 10. Thus, when the phase delay is no longer changing, the condition of the laminate is no longer changing, indicating that the curing process is completed. In the example depicted in FIG. 10 the completion stage of the curing process is marked with an X, corresponding to a time of about 160 minutes.

Diagnostic layer 10 therefore provides a reliable method of defining the completion of the curing process for laminates which contain layer 10. By reliably determining the completion of the cure cycle of laminates, a more standardized product can be produced in less time, and with lower energy consumption and lower costs, as compared with prior art laminate manufacturing processes in which curing cannot be reliably monitored.

Figure 11:
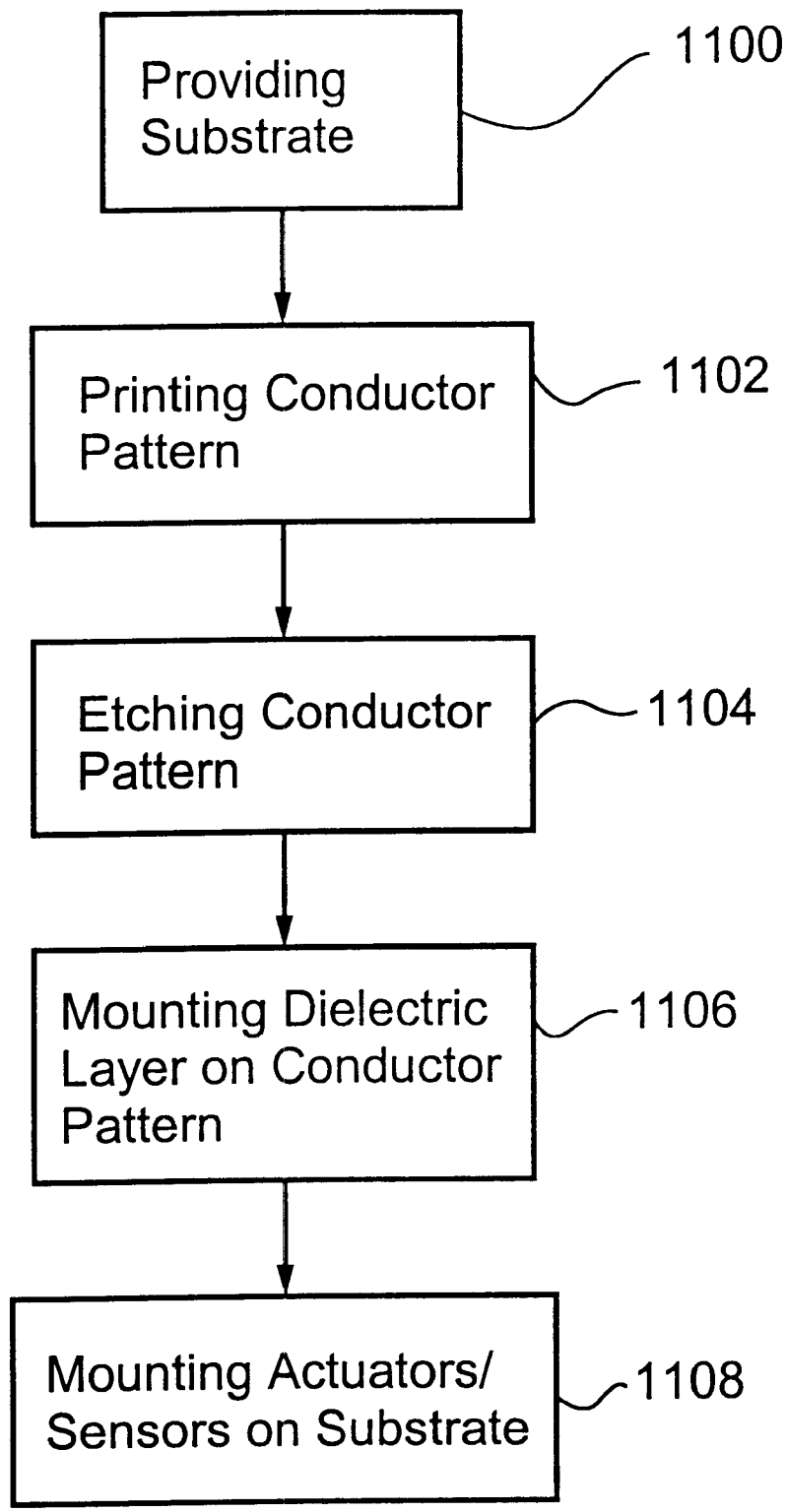
FIG. 11 outlines a series of steps involved in a method of making a diagnostic layer, according to the invention.

FIG. 11 outlines a series of steps involved in a method of making a diagnostic layer of the present invention. The method outlined in FIG. 11 includes features similar to steps involved in production of flexible printed circuits in the electronics industry. Methods of the invention are adapted to be compatible with both the characteristics and components of diagnostic layer 10 of the invention, and with laminate/composite manufacturing processes. Step 1100 of FIG. 11 involves providing a dielectric substrate for the diagnostic layer. A dielectric substrate provided in step 1100 is preferably resistant to both high and low temperatures, and has a preferred thickness in the range of from about 0.001 to 0.010 inches. More preferably the dielectric substrate has a thickness in the range of from about 0.001 to 0.005 inches. Most preferably the dielectric substrate has a thickness in the range of from about 0.001 to 0.003 inches. A currently preferred dielectric substrate is a polyimide film, such as various types of Kapton® available from DuPont (Circleville, Ohio).

Step 1102 of FIG. 11 involves printing a conductor pattern on the dielectric substrate. Step 1104 involves etching a conductor pattern on the dielectric substrate according to the pattern printed in step 1102. Step 1106 involves mounting a second dielectric layer on the dielectric substrate provided in step 1100. A preferred second dielectric layer is a layer of Kapton® of suitable thickness. Step 1108 involves mounting a plurality of actuators/sensors on the dielectric substrate such that electrical contact is made with the conductor etched in step 1104. Preferably, each actuator/sensor mounted on the dielectric substrate is a piezoelectric device which can function both as an actuator and as a sensor. Most preferably, each actuator/sensor mounted on the dielectric substrate is a piezoceramic. Prior to mounting actuators/sensors on the dielectric substrate in step 1108, a hole may be punched in the second dielectric layer at each location at which an actuator/sensor is to be mounted.

Diagnostic layer 10 of the invention, produced according to the methods described herein, may be incorporated in or on a laminate or other structure, generally according to methods well known in the art, with no loss in strength or structural integrity of the resulting laminate (FIGS. 8 and 9), and generally no modification to the original manufacturing (curing) process. Diagnostic layer 10 can simply be treated as one additional ply in the laminate.

Figure 12:
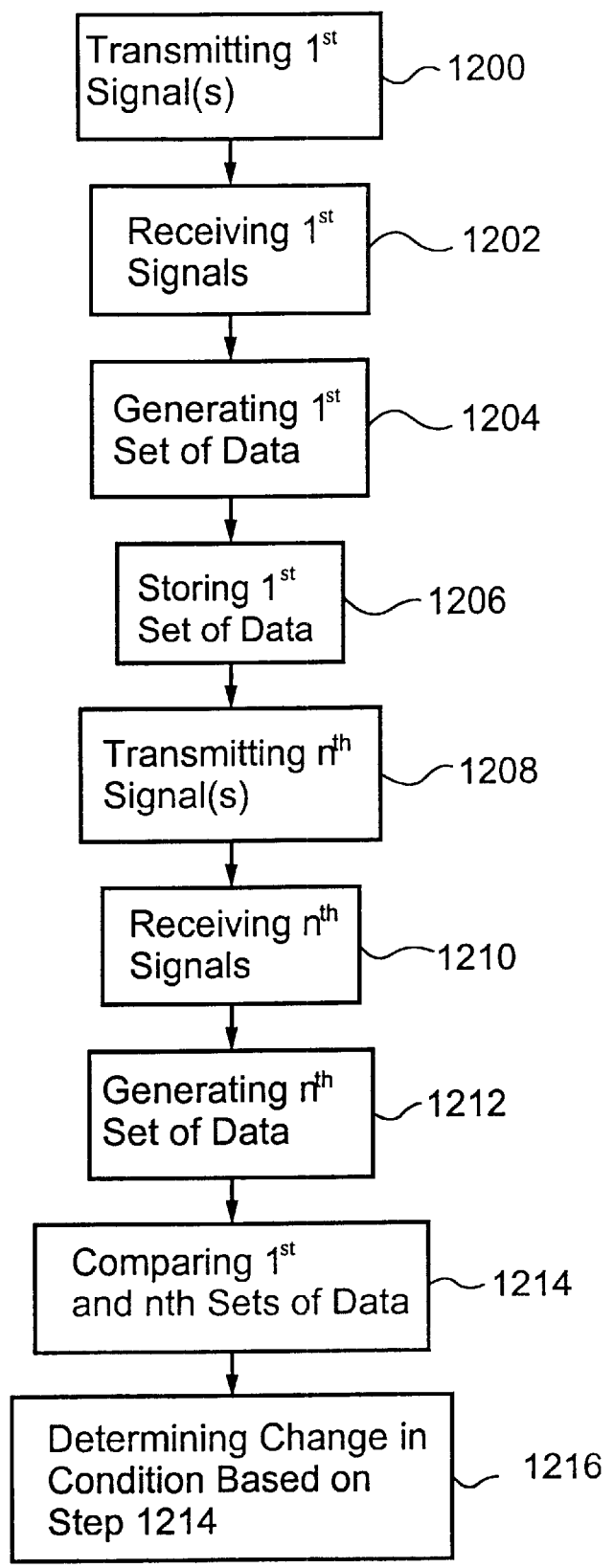
FIG. 12 schematically represents steps involved in a method of monitoring the condition of a diagnostic layer, according to the invention.

FIG. 12 outlines a series of steps involved in a method of diagnosing a change having occurred in the condition of a diagnostic layer 10 or diagnostic unit 20/20', according to another embodiment of the invention. Step 1200 involves transmitting a first input signal to at least one actuator of a diagnostic layer or diagnostic unit. Step 1202 involves receiving a first set of output signals from a plurality of sensors in the diagnostic layer, in response to the first input signal. Step 1204 involves generating a first set of diagnostic data corresponding to the first set of output signals, wherein the first set of diagnostic data is representative of a first structural condition of the diagnostic layer or unit at a first time point. Step 1206 involves storing the first set of data, e.g., in a memory of a computer. Step 1208 involves inputting a second or $n^{th}$ signal to at least one actuator of the diagnostic layer or diagnostic unit, wherein the second or $n^{th}$ input signal is input at a time point later than the first time point. Step 1210 involves receiving a second or $n^{th}$ set of output signals from a plurality of sensors in the diagnostic layer, in response to the second or $n^{th}$ input signal. Step 1212 involves generating a second or $n^{th}$ set of diagnostic data corresponding to the second or $n^{th}$ set of received signals, wherein the $n^{th}$ set of diagnostic data is representative of a subsequent condition of the diagnostic layer or unit at a time point subsequent to the first time point.

The $n^{th}$ set of data obtained in step 1212 may be stored for later access and analysis. Step 1214 involves comparing the first set of data obtained in step 1204 with the $n^{th}$ set of data obtained in step 1212. Step 1216 involves determining change in condition, if any, of the diagnostic layer or unit during the time period between the acquisition of the first set of diagnostic data (the first time period) and the $n^{th}$ set of diagnostic data (the subsequent time period).

With reference to the description of FIG. 12, the first input signal(s) input to the actuators and the first output signals received from the sensors in response to the first input signal(s) represent signals input and received prior to input and reception of the $n^{th}$ signals; and the first set of data represents a set of diagnostic data obtained prior to obtaining the $n^{th}$ set of diagnostic data. The method may also be carried out without steps 1204 and 1212.

Additional input signals may be input to the diagnostic layer, i.e. after input of the $n^{th}$ input signal, and corresponding additional sets of data (e.g., the $(n+x)^{th}$ set) may be obtained after the $n^{th}$ set of data has been acquired. Any of the additional set of diagnostic data, e.g., the $(n+x)^{th}$ set, may be compared with any prior set of data, i.e. the first through the $(n+(x-1))^{th}$ set of data, to monitor any further change in condition of the diagnostic layer. In this way, compositions and methods of the invention allow for the on-going monitoring of a diagnostic layer or laminate unit.

Figure 13:
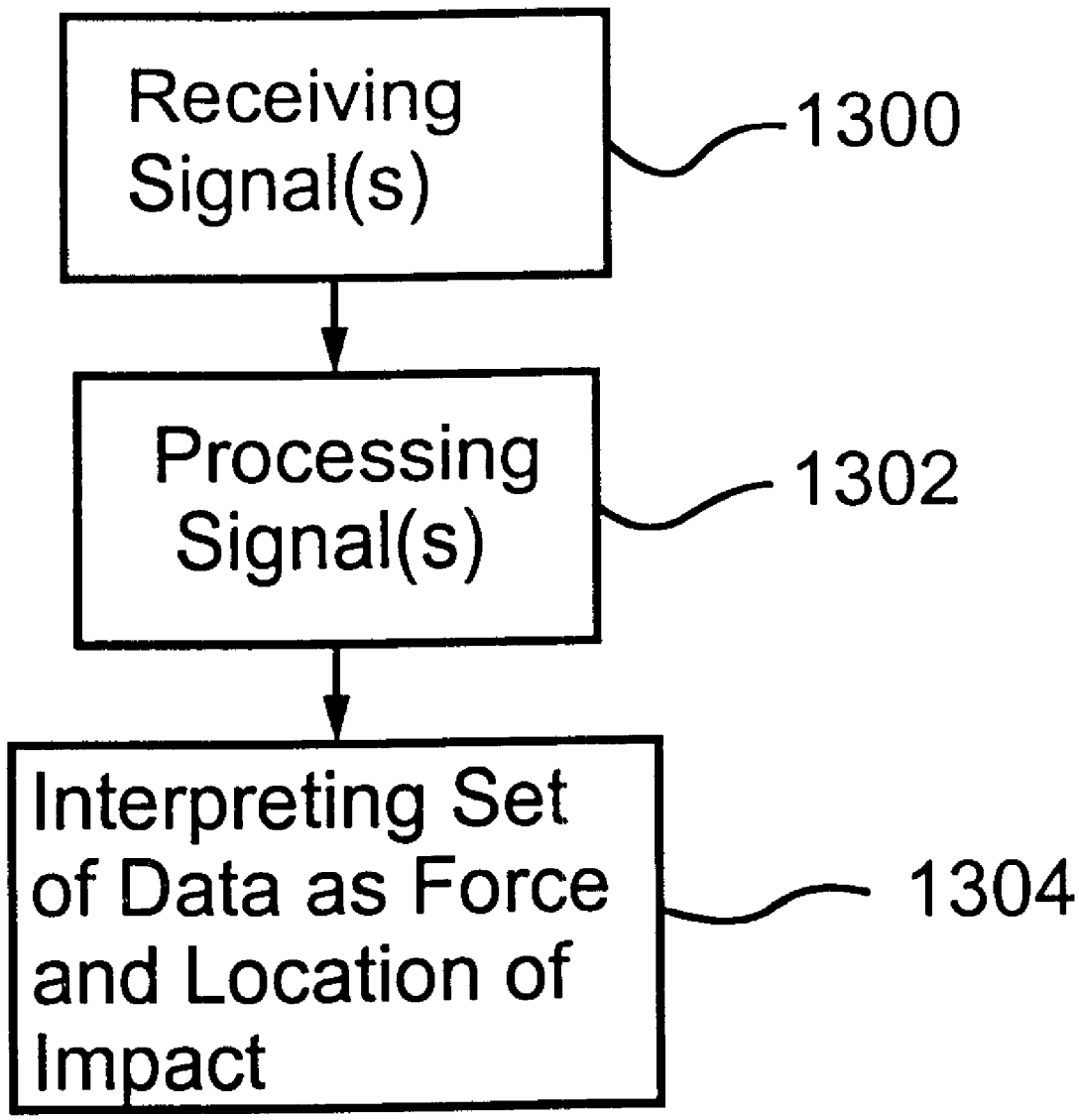
FIG. 13 schematically represents steps involved in a method of monitoring the structural integrity of a structure incorporating a diagnostic layer, according to another embodiment of the invention.

FIG. 13 outlines a series of steps involved in a method of detecting a physical deformation of a structure having a diagnostic layer incorporated therein, according to another embodiment of the invention. The diagnostic layer may have a plurality of actuators/sensors in the form of a network or array. Preferably, the plurality of actuators/sensors are piezoelectric devices, such as piezoceramic actuators/sensors. A piezoelectric sensor in a diagnostic layer having undergone physical deformation emits a diagnostic signal which may be received by, for example, a signal receiving unit. Step 1300 involves the reception of the signal from at least one sensor located in the diagnostic layer. A signal received from the sensor may be in the form of voltage readings. Step 1302 involves processing the signal to generate diagnostic data representative of the physical deformation of the diagnostic layer. Step 1304 involves interpreting the set of diagnostic data as a force and location of the impact.

FIG. 14 outlines a series of steps involved in a method of curing a laminate material including a diagnostic layer, wherein step 1400 involves providing an uncured laminate material including a diagnostic layer. Step 1402 involves subjecting the uncured laminate material to a heat cycle in which the temperature is raised above ambient temperature to an elevated temperature that initiates curing, and maintained above ambient temperature until curing is complete, after which time the temperature may be lowered. Step 1404 involves monitoring changes in the condition of the diagnostic layer of the laminate material until the condition of the diagnostic layer remains substantially constant. When the condition of the diagnostic layer of the laminate material becomes substantially constant, the temperature to which the laminate material is exposed may be lowered. In particular, step 1404 involves monitoring changes in the condition of the diagnostic layer of the laminate material by monitoring the phase shift of a diagnostic signal input to the diagnostic layer until the phase shift attains a substantially constant value.

It will be clear to one skilled in the art that the above embodiment may be altered in many ways without departing from the scope of the invention. Accordingly, the scope of the invention should be determined by the following claims and their legal equivalents.

What is claimed is:

1. A diagnostic layer for detecting a structural condition of a material, said diagnostic layer comprising:
   a thin and flexible dielectric substrate having embedded therein:
      a network of actuators/sensors spatially distributed such that at least two actuators/sensors detect a propagating stress wave generated by at least one other actuators/sensors, wherein said actuators/sensors capable of generating electrical signals representative of a structural condition of said material;
      a plurality of conductive elements electrically interconnecting said actuators/sensors; and
      an output lead electrically connected to said conductive elements.

2. The diagnostic layer of claim 1, wherein said actuators/sensors are spatially distributed such that each of said actuators/sensors detects propagating stress waves generated by at least two other actuators/sensors.

3. The diagnostic layer of claim 1, wherein said actuators/sensors are piezoelectric sensors and generate said electrical signals in response to physical deformations of said piezoelectric sensors.

4. A diagnostic system for detecting a structural condition of a material, said diagnostic system comprising:
   a diagnostic layer comprising:
      a thin and flexible dielectric substrate having embedded therein:
         a network of actuators/sensors spatially distributed such that at least two actuators/sensors detect a propagating stress wave generated by at least one other actuators/sensors;
         a plurality of conductive elements electrically interconnecting said actuators/sensors; and
         an output lead electrically connected to said conductive elements;
   a signal receiving means electrically coupled to said output lead for receiving said output signals from said actuators/sensors; and
   an interfacing means in electrical communication with said signal receiving means, said interfacing means comprising a processing means for processing said output signals and generating data representing said structural condition of said material.

5. The diagnostic system of claim 4, further comprising a signal generating means electrically connected to said output lead for providing an input signal to said at least one other actuators/sensors.

6. The diagnostic system of claim 5, wherein said signal generating means is electrically connected to said interfacing means, said interfacing means further comprises a control means for controlling said input signal to said at least one other actuators/sensors.

7. The diagnostic system of claim 5, further comprising a network of actuators/sensors spatially distributed such that each of said actuators/sensors detects propagating stress waves generated by at least two other actuators/sensors.

8. The diagnostic system of claim 4, wherein said actuators/sensors are piezoelectric sensors and generate said output signals in response to physical deformations of said piezoelectric sensors.

9. The diagnostic system of claim 4, wherein said signal receiving means is electrically coupled to said output lead by wireless means.

10. The diagnostic system of claim 4, wherein said interfacing means further comprises a memory means for storing data from said signal receiving means.

11. The diagnostic system of claim 4 wherein said structural condition comprises a location and a size of structural damage in said diagnostic layer.

12. The diagnostic system of claim 4 wherein said structural condition comprises a location and a force of an impact to said diagnostic layer.

13. The diagnostic system of claim 4 wherein said structural condition comprises progression of curing.

14. A method for detecting a change in a structural condition of a material, said method comprising the steps of:
   a) providing said material a diagnostic layer, said diagnostic layer comprising:
      a thin and flexible dielectric substrate having embedded therein:
         a network of actuators/sensors spatially distributed such that at least two actuators/sensors detect a propagating stress wave generated by at least one other actuators/sensors;
         a plurality of conductive elements electrically interconnecting said actuators/sensors; and
         an output lead electrically connected to said conductive elements;
   b) transmitting a first input signal to said at least one other actuators/sensors through said output lead;
   c) receiving a first set of output signals from said at least two actuators/sensors in response to said first input signal;
   d) subsequently transmitting a second input signal to said at least one other actuators/sensors through said output lead;
   e) receiving a second set of output signals from said at least two actuators/sensors in response to said second input signal; and
   f) analyzing said first set of output signals and said second set of output signals to determine a difference between said first set of output signals and said second set of output signals, wherein said difference represents said change in said structural condition.

15. The method of claim 14, wherein step (f) further comprises generating a first set of data from said first set of output signals and generating a second set of data from said second set of output signals, wherein set first set of data represents a first structural condition of said material and said second set of data represents a second structural condition of said material.

16. The method of claim 14 wherein said change in said structural condition comprises a location and a size of damage in said diagnostic layer.

17. The method of claim 14 wherein said change in said structural condition comprises progression of curing.

18. The method of claim 14, further comprising the steps of:
- a) subsequently transmitting an $n^{th}$ input signal to said at least one other actuators/sensors through said output lead;
- b) receiving an $n^{th}$ set of output signals from said at least two actuators/sensors in response to said $n^{th}$ input signal; and
- c) analyzing said $n^{th}$ set of output signals and a prior set of output signals to determine a difference between said $n^{th}$ set of output signals and said prior set of output signals, wherein said difference represents a further change in said structural condition of said material; and
- d) repeating steps (a), (b), and (c) for a predetermined time.

19. The method of claim 14, further comprising the step of, before step (a), bonding said diagnostic layer to an external surface of said material.

20. A method for detecting a physical deformation of a material having a diagnostic layer, said diagnostic layer comprising a network of interconnected actuators/sensors spatially distributed on a thin and flexible dielectric substrate and electrically connected to an output lead by a plurality of conductive elements, at least two of said actuators/sensors capable of detecting a structural condition in a region of said material, said method comprising the steps of:
- a) receiving a signal from at least one actuators/sensors of said network, wherein said signal represents a physical deformation of said at least one actuators/sensors of said network; and
- b) processing said signal to generate data representing said physical deformation of said material.

21. The method of claim 20 wherein said sensors are piezoelectric sensors.

22. The method of claim 20 wherein said physical deformation of said material comprises an impact on said material and said data comprise a force and a location of said impact.

23. The diagnostic layer of claim 3, wherein said interconnected actuators/sensors are piezoceramic sensors.

24. A diagnostic layer for detecting a structural condition of a material, said diagnostic layer comprising:
a thin and flexible dielectric substrate having embedded therein:
- a network of actuators/sensors spatially distributed on said substrate, said actuators/sensors capable of generating electrical signals representative of a structural condition of said material, wherein at least two actuators/sensors detect a structural condition in a region of said material;
- a plurality of conductive elements electrically interconnecting said actuators/sensors; and
- an output lead electrically connected to said conductive elements.

25. The diagnostic layer of claim 24, wherein said actuators/sensors are piezoelectric sensors and generate said electrical signals in response to physical deformations of said piezoelectric sensors.

26. The diagnostic layer of claim 25, wherein said actuators/sensors are piezoceramic sensors.

* * * * *

UNITED STATES PATENT AND TRADEMARK OFFICE
CERTIFICATE OF CORRECTION

| | | |
|---|---|---|
| PATENT NO. | : 6,370,964 B1 | Page 1 of 1 |
| APPLICATION NO. | : 09/447480 | |
| DATED | : April 16, 2002 | |
| INVENTOR(S) | : Chang et al. | |

It is certified that error appears in the above-identified patent and that said Letters Patent is hereby corrected as shown below:

Column 1, line 11-16 insert the following:

-- FEDERALLY-SPONSORED RESEARCH OR DEVELOPMENT
This invention was made with Government support under contract DAAH04-95-1-0611 awarded by the Department of the Army. The Government has certain rights in this invention. --

Signed and Sealed this
Sixth Day of March, 2012

David J. Kappos
*Director of the United States Patent and Trademark Office*